United States Patent [19]
Blenk et al.

[11] Patent Number: 5,965,797
[45] Date of Patent: *Oct. 12, 1999

[54] BACTERIAL GENES

[76] Inventors: Robert G Blenk, 745 S. Bernardo Ave., Apt 271D, Sunnyvale, Calif. 94087; Susan Ely, 64 Newfield Gardens, Marlow, Bucks SL7 1JP, United Kingdom; Ravindra Haribhai Tailor, 50 Nettlecombe, Bracknell, Berkshire RG12 3UQ, United Kingdom; Janet Mary Tippett, 25 Savernake, Tilehurst, Reading RG3 4LY, United Kingdom

[*] Notice: This patent is subject to a terminal disclaimer.

[21] Appl. No.: 08/460,570

[22] Filed: Jun. 2, 1995

Related U.S. Application Data

[62] Division of application No. 07/520,228, May 9, 1990, Pat. No. 5,573,766.

[30] Foreign Application Priority Data

May 9, 1989 [GB] United Kingdom .................. 8910624

[51] Int. Cl.[6] ........................... C12N 5/14; C12N 15/32; C12N 1/21

[52] U.S. Cl. .................. 800/302; 435/69.1; 435/252.1; 435/252.31; 435/320.1; 435/410; 435/440; 435/468; 435/471; 536/23.1; 536/23.71; 424/93.2; 424/93.461

[58] Field of Search ............................. 435/69.1, 252.31, 435/410, 412, 420, 424, 172.3, 320.1, 252.1, 440, 471, 468; 536/23.71; 800/205, 235, 302; 514/44; 424/93.2, 93.461; 576/23.71

[56] References Cited

PUBLICATIONS

Aronson et al, Microbiol. Rev. 50(i): 1–24 1986.

*Primary Examiner*—John L. LeGuyader
*Attorney, Agent, or Firm*—Cushman Darby & Cushman IP Group of Pillsbury Madison & Sutro LLP

[57] ABSTRACT

Novel strains of the insecticidal microorganism *Bacillus thuringiensis* are described. These contain novel genes, and in particular a gene coding for a novel insecticidal endotoxin, 81 kiloDaltons in length, toxic to both Lepidoptera and Coleoptera. The novel strains and the genes they contain may be used to combat insect attack against plants.

11 Claims, 26 Drawing Sheets

```
N            M                          H
D            S                          P
E            E                          H          C   T
1            1                          1          L   A
                                                   A   Q
                                                   1   1
CAT ATG TAT AGA GCA ACT TAA TCA AGC AGA GAT ATT TTC ACC TAT CGA    48
His Met Tyr Arg Ala Thr Ter Ser Ser Arg Asp Ile Phe Thr Tyr Arg
  1           5              10              15

TGA AAA TAT CTC TGC TTT TTC TTT TAT TTG GTA TAT GCT TTA CTT       96
Ter Lys Tyr Leu Cys Phe Phe Phe Tyr Leu Val Tyr Ala Leu Leu
       20              25              30

A
       T
       Q
       1
GTA ATC GAA AAT AAA GCA CTA ATA AGA GTA TTT ATA GGT GTT TGA AGT  144
Val Ile Glu Asn Lys Ala Leu Ile Arg Val Phe Ile Gly Val Ter Ser
           35              40              45

FIG. 5A
```

```
                    MD          MD       M      M
                    SR          SR       A      S
                    EA          EA       E      E
                    11          11       2      1
TAT TTC AGT TCA TTT TTA AAG AAG GTT TAA AGA CGT TAG AAA GTT ATT    192
Tyr Phe Ser Ser Phe Leu Lys Lys Val Ter Arg Arg Ter Lys Val Ile
    50              55              60

S                                  AM                    AD
         S                                  SS                    LD
         P                                  EE                    UE
         1                                  11/                   11
AAG GAA TAA TAT TTA GTA AAT TCC ACA TAT ATT ATA TAA TTA ATT        240
Lys Glu Ter Tyr Leu Val Asn Ser Thr Tyr Ile Ile Ter Leu Ile
65           70              75              80

ATG AAA TAT ATG TAT AAA TTG AAA ATG CTT TAT TTG ACA TTA CAG CTA    288
Met Lys Tyr Met Tyr Lys Leu Lys Met Leu Tyr Leu Thr Leu Gln Leu
            85              90              95
```

FIG. 5B

```
                                                                                    M
                                                                                    N
                                                                                    L
                                          M                                         1
                                          S
                                          E
                                          1
AGT ATA ATT TTG TAT GAA TAA AAT TAT ATC TGA AAA TTA AAT AAT AGT     336
Ser Ile Ile Leu Tyr Glu Ter Asn Tyr Ile Ter Lys Leu Asn Asn Ser
        100                 105                 110

A M
                        S S
                        E E
                        1 1
            S           /
            B
            O
            1
ATA AGT GGA GGG ATT AAT ATG AAA CTA AAG AAT CAA GAT AAG CAT CAA     384
Ile Ser Gly Gly Ile Asn Met Lys Leu Lys Asn Gln Asp Lys His Gln
        115                 120                 125

M                                           H
        A                                           N
        E                                           F
        1                                           1
S
F
A
N
AGT TTT TCT AGC AAT GCG AAA GTA GAT AAA ATC TCT ACG GAT TCA CTA     432
Ser Phe Ser Ser Asn Ala Lys Val Asp Lys Ile Ser Thr Asp Ser Leu
        130                 135                 140
```

FIG. 5C

```
                                                        AM   B  N
                                                        SS   S  L
                                                        EE   P  A
                                                        11   H  3
                                                         /
AAA AAT GAA ACA GAT ATA GAA TTA CAA AAC ATT AAT CAT GAA GAT TGT    480
Lys Asn Glu Thr Asp Ile Glu Leu Gln Asn Ile Asn His Glu Asp Cys
145                 150                 155                 160

M       D
    B       D
    O       E
    2       1

TTG AAA ATG TCT GAG TAT GAA AAT GTA GAG CCG TTT GTT AGT GCA TCA    528
Leu Lys Met Ser Glu Tyr Glu Asn Val Glu Pro Phe Val Ser Ala Ser
                165                 170                 175

BAN RKS ASN
    S                                           ASL SPT WEA
    F                                           NPA ANY RCE
    A                                           114 111 211
    N                                            /   /   ///

ACA ATT CAA ACA GGT ATT GGT ATT GCG GGT AAA ATA CTT GGT ACC CTA    576
Thr Ile Gln Thr Gly Ile Gly Ile Ala Gly Lys Ile Leu Gly Thr Leu
            180                 185                 190
```

GGC GTT CCT TTT GCA GGA CAA GTA GCT AGT CTT TAT AGT TTT ATC TTA   624
Gly Val Pro Phe Ala Gly Gln Val Ala Ser Leu Tyr Ser Phe Ile Leu
     195                 200                 205

A    HH  HMD                                                       A
           L    AP  ASD                                                       F
           V    EH  ETE                                                       L
           1    11  321                                                       3
                    ///
GGT GAG CTA TGG CCT AAG GGG AAA AAT CAA TGG GAA ATC TTT ATG GAA   672
Gly Glu Leu Trp Pro Lys Gly Lys Asn Gln Trp Glu Ile Phe Met Glu
     210                 215                 220

NNK  E              AM   M
     SLS  A              SS   B
     PAP  R              EE   O
     H32  1              11   2
     ///                 //
CAT GTA GAA GAG ATT ATT AAT CAA AAA ATA TCA ACT TAT GCA AGA AAT   720
His Val Glu Glu Ile Ile Asn Gln Lys Ile Ser Thr Tyr Ala Arg Asn
     225                 230                 235                 240
```

AAA GCA CTT ACA GAC TTG AAA GGA TTA GGA GAT GCC TTA GCT GTC TAC            768
Lys Ala Leu Thr Asp Leu Lys Gly Leu Gly Asp Ala Leu Ala Val Tyr
         245                 250                 255

NH      H                                                                  M
LN      N                                                                  A
AF      F                                                                  E
31      3                                                                  1
 /
CAT GAT TCG CTT GAA AGT TGG GTT GGA AAT CGT AAT AAC ACA AGG GCT            816
His Asp Ser Leu Glu Ser Trp Val Gly Asn Arg Asn Asn Thr Arg Ala
         260                 265                 270

AGG AGT GTT GTC AAG AGC CAA TAT ATC GCA TTA GAA TTG ATG TTC GTT            864
Arg Ser Val Val Lys Ser Gln Tyr Ile Ala Leu Glu Leu Met Phe Val
         275                 280                 285
```

FIG. 5F

```
                                                     B  ANR  K
                                                     A  SLS  P
                             M  AM                   N  PAA  N
                             N  LN                   1  141  1
                             L  WL                      / /
                             1  H1
CAG AAA CTA CCT TCT TTT GCA GTG TCT GGA GAG GAG GTA CCA TTA TTA        912
Gln Lys Leu Pro Ser Phe Ala Val Ser Gly Glu Glu Val Pro Leu Leu
    290             295             300

B               A F                           M
    B               L N                           S
    V               U U                           E
    1               1 H                           1
CCG ATA TAT GCC CAA GCT GCA AAT TTA CAT TTG CTA TTA AGA GAT            960
Pro Ile Tyr Ala Gln Ala Ala Asn Leu His Leu Leu Leu Arg Asp 320
305             310             315

N A             S                 M
    S V             F                 B
    1 A             A                 O
    1 3             N                 2
     /
GCA TCT ATT TTT GGA AAA GAG TGG GGA TTA TCA TCT TCA GAA ATT TCA        1008
Ala Ser Ile Phe Gly Lys Glu Trp Gly Leu Ser Ser Ser Glu Ile Ser
            325             330             335

FIG.5G
```

```
                                                                        1056
                                              T
                                              A
                                              Q
                                              1
ACA TTT TAT AAC CGT CAA GTC GAA CGA GCA GGA GAT TAT TCC TAC CAT
Thr Phe Tyr Asn Arg Gln Val Glu Arg Ala Gly Asp Tyr Ser Tyr His
         340             345             350

E         M                       R
                        C         N                       S
                        P         L                       A
                        1         1                       1
                                                                        1104
TGT GTG AAA TGG TAT AGC ACA GGT CTA AAT AAC TTG AGG GGT ACA AAT
Cys Val Lys Trp Tyr Ser Thr Gly Leu Asn Asn Leu Arg Gly Thr Asn
         355             360             365

R                       B               N       M
            S                       S               L       S
            A                       M               A       E
            1                       2               3       1
                                                                        1152
GCC GAA AGT TGG GTA CGA TAT AAT CAA TTC CGT AGA GAC ATG ACT TTA
Ala Glu Ser Trp Val Arg Tyr Asn Gln Phe Arg Arg Asp Met Thr Leu
         370             375             380
```

ATG GTA CTA GAT TTA GTG GCA CTA TTT CCA AGC TAT GAT ACA CAA ATG   1200
Met Val Leu Asp Leu Val Ala Leu Phe Pro Ser Tyr Asp Thr Gln Met
385                 390                 395                 400

M                                         S
         S                      HF   F  R          F
         E                      GO   I  S          A
         1                      AK   N  A          N
                                11   1  1          1

TAT CCA ATT AAA ACT ACA GCC CAA CTT ACA AGA GAA GTA TAT ACA GAC   1248
Tyr Pro Ile Lys Thr Thr Ala Gln Leu Thr Arg Glu Val Tyr Thr Asp
                    405                 410                 415

F                                              R
         O                                              S
         K                                              A
         1                                              1

GCA ATT GGG ACA GTA CAT CCG CAT CCA AGT TTT ACA AGT ACG ACT TGG   1296
Ala Ile Gly Thr Val His Pro His Pro Ser Phe Thr Ser Thr Thr Trp
                    420                 425                 430
```

FIG. 5I

```
                                              BglI  BmN   BfN   EC   EA
                                              1     1     U     1    S U
                                                          H     5    2

TAT AAT AAT AAT GCA CCT TCG TTC TCT GCC ATA GAG GCT GCT GTT    1344
Tyr Asn Asn Asn Ala Pro Ser Phe Ser Ala Ile Glu Ala Ala Val Val
    435                 440                 445

TaqI    TspAI    XmaI     MaeI              DdeI         MkL
            AflII    BanI     AflIII                         1
            QaI      1N       1
            1

CGA AAC CCG CAT CTA CTC GAT TTT CTA GAA CAA GTT ACA ATT TAC AGC    1392
Arg Asn Pro His Leu Leu Asp Phe Leu Glu Gln Val Thr Ile Tyr Ser
    450                 455                 460

MseI        MaeIII
    1           3

TTA TTA AGT CGA TGG AGT AAC ACT CAG TAT ATG AAT ATG TGG GGA GGA    1440
Leu Leu Ser Arg Trp Ser Asn Thr Gln Tyr Met Asn Met Trp Gly Gly    480
465                 470                 475

FIG.5J
```

```
                                                                                      1488
                                        M   M
                                        A   S
                               M        E   E
                               N        2   1
                               L
                               1
           M  E
           A  C
           E  R
           1  1
CAT AAA CTA GAA TTC CGA ACA ATA GGA GGA ACG TTA AAT ATC TCA ACA
His Lys Leu Glu Phe Arg Thr Ile Gly Gly Thr Leu Asn Ile Ser Thr
            485                 490                 495

1536
                           M
     A M                   A
     S S                   E
     E E                   3
     1 1
  B  X M D
  1  H B P
  N  O O N
  1  2 1 1
CAA GGA TCT ACT AAT ACT TCT ATT AAT CCT GTA ACA TTA CCG TTC ACT
Gln Gly Ser Thr Asn Thr Ser Ile Asn Pro Val Thr Leu Pro Phe Thr
            500                 505                 510

1584
                    H                         H
                    N                         N
                    F                         F
                    1                         1
  X A  T B  A M  A
  H V  A S  H A  A
  O A  Q M  A E  T
  1 1  1 2  2 2  2
TCT CGA GAC GTC TAT AGG ACT GAA TCA TTG GCA GGG CTG AAT CTA TTT
Ser Arg Asp Val Tyr Arg Thr Glu Ser Leu Ala Gly Leu Asn Leu Phe
            515                 520                 525

FIG.5K
```

```
                        M           R  SAS M      S           F
                        S           S  TVE A      P           O
                        E           A  YRC E      O           K
                        1           1  121 1      1           1
                                       / /                             1632
TTA ACT CAA CCT GTT AAT GGA GTA CCT AGG GTT GAT TTT CAT TGG AAA
Leu Thr Gln Pro Val Asn Gly Val Pro Arg Val Asp Phe His Trp Lys
530             535             540

M   DP                                  S       TE  SAS
    B   PV                                  F       TC  EPC
    A   NU                                  A       HR  CYR
    E   11                                  N       22  111
    3                                                  //       1680
TTC GTC ACA CAT CCG ATC GCA TCT GAT AAT TTC TAT TAT CCA GGG TAT
Phe Val Thr His Pro Ile Ala Ser Asp Asn Phe Tyr Tyr Pro Gly Tyr
545             550             555             560

F   H   H
        I   G   N
        N   A   F
        1   1   1
                                                                 1728
GCT GGA ATT GGG ACG CAA TTA CAG GAT TCA GAA AAT GAA TTA CCA CCT
Ala Gly Ile Gly Thr Gln Leu Gln Asp Ser Glu Asn Glu Leu Pro Pro
565             570             575
```

FIG. 5L

```
GAA GCA ACA GGA CAG CCA AAT TAT GAA TCT TAT AGT CAT AGA TTA TCT    1776
Glu Ala Thr Gly Gln Pro Asn Tyr Glu Ser Tyr Ser His Arg Leu Ser
    580                         585                         590

P  H              A  S
              L  N              F  F  A
              E  F              L  N  P  N
              1  1              3  N  A  H3
                                         //

CAT ATA GGA CTC ATT TCA GCA TCA CAT GTG AAA GCA TTG GTA TAT TCT    1824
His Ile Gly Leu Ile Ser Ala Ser His Val Lys Ala Leu Val Tyr Ser
    595                         600                         605

H  S  M  D  R
              G  F  B  P  S
              A  A  O  N  A
              1  N  1  1  1

TGG ACG CAT CGT AGT GCA GAT CGT ACA AAT ACA ATT GAG CCA AAT AGC    1872
Trp Thr His Arg Ser Ala Asp Arg Thr Asn Thr Ile Glu Pro Asn Ser
    610                         615                         620
```

ATT ACA CAA ATA CCA TTA GTA AAA GCT TTC AAT CTG TCT TCA GGT GCC   1920
Ile Thr Gln Ile Pro Leu Val Lys Ala Phe Asn Leu Ser Ser Gly Ala
625                 630                 635                 640

A A E         A S                     E         A   T
       V S C         P C                     C         S   A
       A U R         Y R                     R         U   Q
       2 1 2         1 1                     V         2   1
           /           /                                    /
    N M       R  S
    S N       B  A
    P L       O  1
    B 1       2
GCT GTA GTG AGA GGA CCA GGA TTT ACA GGT GGG GAT ATC CTT CGA AGA   1968
Ala Val Val Arg Gly Pro Gly Phe Thr Gly Gly Asp Ile Leu Arg Arg
                645                 650                 655

S   A M
                                      S   S S
                                      P   E E
                                      1   1 1
                                            /
     H       M   R
     N       B   S
     F       O   A
     3       2   1
ACG AAT ACT GGT ACA TTT GGG GAT ATA CGA GTA AAT ATT AAT CCA CCA   2016
Thr Asn Thr Gly Thr Phe Gly Asp Ile Arg Val Asn Ile Asn Pro Pro
                660                 665                 670
```

FIG. 5N

```
                                EMR    TH    HN    HN
                                CL     HA    NF    NF
                                RV     A1    F1    F3
                                1      1
TTT GCA CAA AGA TAT CGC GTG AGG ATT CGC TAT GCT TCT ACC ACA GAT    2064
Phe Ala Gln Arg Tyr Arg Val Arg Ile Arg Tyr Ala Ser Thr Thr Asp
675                 680                 685

MAE   MSE                   A    AM
                    2     1                     L    SS
                                                U    EE
                                                1    11
TTA CAA TTC CAT ACG TCA ATT AAC GGT AAA GCT ATT AAT CAA GGT AAT    2112
Leu Gln Phe His Thr Ser Ile Asn Gly Lys Ala Ile Asn Gln Gly Asn
            690                 695                 700

MNL       MNL       DDE
            1         1         1
TTT TCA GCA ACT ATG AAT AGA GGA GAG GAC TTA GAC TAT AAA ACC TTT    2160
Phe Ser Ala Thr Met Asn Arg Gly Glu Asp Leu Asp Tyr Lys Thr Phe
705                 710                 715                 720
```

FIG. 50

```
                                             A       R           R S A   2208
                                             L       S A         S A 1
                                             U       A 1         1
                                             1
AGA ACT GTA GGC TTT ACC ACT CCA TTT AGC TTT TTA GAT GTA CAA AGT
Arg Thr Val Gly Phe Thr Thr Pro Phe Ser Phe Leu Asp Val Gln Ser
        725                 730                 735

K  EM
                         M               S  AA
                         B               P  RE
                         O               2  13
                         2                  //
ACA TTC ACA ATA GGT GCT TGG AAC TTC TCT TCA GGT AAC GAA GTT TAT  2256
Thr Phe Thr Ile Gly Ala Trp Asn Phe Ser Ser Gly Asn Glu Val Tyr
        740                 745                 750

X   H   M       M  N
                         M   P   A       N  D
                         N   A   E       L  E
                         1   2   3       1  1

ATA GAT AGA ATT GAA TTT GTT CCG GTA GAA TTT GTA ACA TAT GAG GCA GAA  2304
Ile Asp Arg Ile Glu Phe Val Pro Val Glu Val Thr Tyr Glu Ala Glu
        755                 760                 765
```

TAT GAT TTT GAA AAA GCG CAA GAG AAG GTT ACT GCA CTG TTT ACA TCT        2352
Tyr Asp Phe Glu Lys Ala Gln Glu Lys Val Thr Ala Leu Phe Thr Ser
770                 775                 780

H H M                   M                                                      E
                    M N N                   S                                                      C
                    F F L                   E                                                      R
                    3 1 1                   1                                                      2

ACG AAT CCA AGA GGA TTA AAA ACA GAT GTA AAG GAT TAT CAT ATT GAC        2400
Thr Asn Pro Arg Gly Leu Lys Thr Asp Val Lys Asp Tyr His Ile Asp
785                 790                 795                 800

H           B P                                                    E
                                N           S L                                                    C
                                F           M E                                                    R
                                1           2 1                                                    1

A S
         P C
         Y R
         1 1

CAG GTA TCA AAT TTA GTA GAG TCT CTA TCA GAT GAA TTC TAT CTT GAT        2448
Gln Val Ser Asn Leu Val Glu Ser Leu Ser Asp Glu Phe Tyr Leu Asp
                805                 810                 815
```

FIG. 5Q

```
                                          T  H
                                          H  A
                                          A  1
                                          1
                        T  H
                        A  N
                        Q  F
                        1  3
GAA AAG AGA GAA TTA TTC GAG ATA GTT AAA TAC GCG AAG CAA CTC CAT   2496
Glu Lys Arg Glu Leu Phe Glu Ile Val Lys Tyr Ala Lys Gln Leu His
                820                 825                 830

M   A     N  N     M
        A   F     S  L     S
        E   L     P  A     E
        3   3     H  3     1
                     /
ATT GAG CGT AAC ATG TAG AAT TAA AAT CTA CCT AAA TCC AGA AAA ATA   2544
Ile Glu Arg Asn Met Ter Asn Ter Asn Leu Pro Lys Ser Arg Lys Ile
                835                 840                 845

R   S
                                S   S
                                A   P
                                1   1
AAA GGG TTA AAT ATA CAA TTC TTG TAC CAA TAT TTT GAG TGA TTA GAT   2592
Lys Gly Leu Asn Ile Gln Phe Leu Tyr Gln Tyr Phe Glu Ter Leu Asp
                850                 855                 860

GTA TGC TAT TTA ACA GTA GAG ATA TTA AAA           2640
                                    Val Cys Tyr Leu Thr Val Glu Ile Leu Lys
                                    875                                 880

M F
                           S O
                           E K
                           1 1

GTA AAT TTA ATT GTA TGC TAT TTA ACA GTA GAG ATA TTA AAA
              Val Asn Leu Ile Val Cys Tyr Leu Thr Val Glu Ile Leu Lys
                              870

A M
                              S S
                              E E
                              1 1 /
              ATA CAT TAG TAT TAA TAG CAT ACA AAC ATA AGA GAG                2688
              Ile His Ter Tyr Ter Ter His Thr Asn Ile Arg Glu
              885                       890                     895

M
  S
  E
  1

GTA GGA TGA AAT TTA ATT GTA TGC TAT TTA ACA GTA GAG ATA TTA AAA
 Val Gly Ter Asn Leu Ile Val Cys Tyr Leu Thr Val Glu Ile Leu Lys
 865

A M
 S S
 E E
 1 1 /
 ATT AAT TTA TCT ATA CAT TAG TAT TAA TAG CAT ACA AAC ATA AGA GAG
 Ile Asn Leu Ser Ile His Ter Tyr Ter Ter His Thr Asn Ile Arg Glu
               885                       890                     895

CAT TGT CTT TTC GTA GGC TAC AAT GCT CTC TAT TTA CTA TTT ATT TTT          2736
 His Cys Leu Phe Val Gly Tyr Asn Ala Leu Tyr Leu Tyr Leu Phe Ile Phe
             900                     905                     910
```

FIG. 5S

```
MBO2                                    MAE2                        DDE1                        FANLUUH1
CTT TTG TAT CTT CAA ATT GAC GTT GTT CTA AGC GTT CTA TTG CAG CTC    2784
Leu Leu Tyr Leu Gln Ile Asp Val Val Leu Ser Val Leu Leu Gln Leu
            915                 920                 925

BBV1
GTC GTT TAG TAT CAT CAA TGT TTG TAT AAA GAG ATG TTT CCA TAG        2832
Val Val Ter Tyr His Gln Cys Leu Tyr Lys Glu Met Phe Pro Ter
            930                 935                 940

FIN1
AAT TAT GTC CCA TTT GAT TTG CTA ATA ATA CTA AAT CTT TAT TTT CAT    2880
Asn Tyr Val Pro Phe Asp Leu Leu Ile Ile Leu Asn Leu Tyr Phe His
            945                 950                 955         960
```

TCT
                                                  Ser
                                                  975
                                              TTT
                                              Phe
                                          GGC
                                          Gly
                                      GAG
                                      Glu
                                  TAT
                                  Tyr
                              ATT
                              Ile
                          GTA
                          Val
                      GAC
                      Asp
                      970
                  TAT                               H A
                  Tyr                               I L
              AAG                                   N U
              Lys                                   3 1
          CAT
          His                                   T
      TAG                                   GCT
      Ter                                   Ala Ser
      M  M                              TAA
      A  N                              Ter
      E  L                          CTG
      2  1                          Leu
                                TCT
                                Ser
                                985
                            ATT
                            Ile
                        TGT
                        Cys
                    TTG
                    Leu
                CCC
                Pro
            AAG
            Lys
            980
        CAA
        Gln
     TAG   CAT
     Ter   His
     965  TTT
     TAG  Phe
     Ter
 GAT
 Asp
 AGT
 Ser
 TAT
 Tyr
```

FIG.5U

BACTERIAL GENES

This is a division of Application Ser. No. 07/520,228, filed May 9, 1990, now U.S. Pat. No. 5,573,766.

The present invention relates to novel bacterial genes, and to novel strains of the bacterium *Bacillus thuringiensis*; and to uses therefor.

The organism *Bacillus thuringiensis* produces a protein crystal endotoxin which kills insect larvae. It is not however toxic to mammals. It is thus very useful as an agricultural insecticide, in particular against Lepidoptera, Coleoptera and Diptera. Strains of *Bacillus thuringiensis* have been used as agricultural insecticides for a number of years.

The most extensively characterised strain of *Bacillus thuringiensis* active against coleopteran pests is *Bacillus thuringiensis* variety (var.) *tenebrionis*, as deposited in the German Collection of Microorganisms (Deutsche Sammlung von Microorganism) under the reference DSM 2603. We have now discovered novel strains of *Bacillus thuringiensis* having generally similar properties to DSM 2803, but distinguished therefrom by specific insecticidal activity against coleopteran larvae of the genus Diabrotica, as well as by toxicity to lepidopteran larvae. The novel properties of these strains appear to arise from novel genes that they contain.

According to the present invention we provide the novel strains JHCC 4835 and JHCC 4353 of *Bacillus thuringiensis*, deposited at the National Collections of Industrial and Marine Bacteria under the accession numbers NCIMB 40091 and 40090, respectively.

We further provide novel δ-endotoxin genes capable of isolation from said strains JHCC 4835 and JHCC 4353. Such genes may be located either on the bacterial chromosome or on a plasmid. In a further aspect, our invention comprises recombinant DNA homologous with the DNA sequence set out in FIGS. 5A–5U hereof and coding for a novel insecticidally-active endotoxin of molecular weight about 81.2 kilodaltons (hereinafter referred to as "the 81 kD endotoxin"). In specific embodiments of our invention, recombinant DNA coding for insect endotoxins has been cloned from *Bacillus thuringiensis* JHCC 4835 into *E. coli* strains BL21/pJH11 and MC1022/pJH12, deposited at the National Collections of Industrial and Marine Bacteria under the accession numbers 40275 and 40278 respectively. The endotoxin gene in the latter deposit is lepidopteran-specific. We further provide recombinant DNA coding for a second lepidopteran-specific endotoxin gene derived from *Bacillus thuringiensis* strain JHCC 4835, which has been deposited in the form of a bacteriophage Lambda EMBL4 clone CL5 with the National Collections of Industrial and Marine Bacteria under the accession number 40279.

Recombinant DNA according to our invention may comprise genes of varying lengths encoding insecticidally-active proteins. When cloning DNA from the bacterial chromosome it is convenient to use bacteriophage Lambda vectors or other cloning vectors that sequester the recombinant DNA from host cell enzymes that might cause homologous recombination.

We further provide novel insecticidal compositions characterised in that they contain the δ-endotoxin produced by said strains JHCC 4835, JHCC 4353 and *E. coli* BL21/pJH11, and a method of protecting plants from insect attack which comprises exposing the larvae to a δ-endotoxin produced by the said strains JHCC 4353, JHCC 4835 and *E. coli* BL21/pJH11.

The strains JHCC 4835 and JHCC 4353 were soil isolates from Marshall, Iowa, U.S.A. and Dallas, Iowa, U.S.A. respectively. In colony morphology they are generally similar to DSM 2803, and to strain HD-1 which is insecticidal to lepidopteran larvae.

The morphology of the strains of the invention is compared with that of known strains in Table 1.

Biochemical properties of the new and the known strains are compared in Tables 2–4. It will be seen that there are many similarities between the strains.

In view of these biochemical similarities it is surprising that the gene encoding the 81 kD endotoxin in *E. coli* BL21/pJH11 shows very little DNA sequence homology to the *B. thuringiensis* var. *tenebrionis* endotoxin gene of DSM 2803. Use of the coding sequence for the *B. thuringiensis* var. *tenebrionis* endotoxin gene as a DNA probe under relatively mild stringency conditions (3×Standard Saline Citrate at 37° C.) is not sufficient to generate a signal from the coding sequences for this endotoxin gene in strains JHCC 4835 and JHCC 4353. Similarly, use of the coding sequence for the lepidopteran-specific CryIA(c) (this system of nomenclature is described by Höfte and Whitely in Microbiol. Reviews, 53, 1989 at pages 242–255) endotoxin gene from a *Bacillus thuringiensis* var. *kurstaki* strain is not sufficient to generate a DNA hybridisation signal from the coding sequence for the 81 kD endotoxin. Also, use of the novel gene coding sequence as a DNA probe does not generate a hybridisation signal from the *tenebrionis* gene or the three CryIA genes.

The newly-discovered *B. thuringiensis* strains JHCC 4853 and JHCC 4353 show a significantly different specificity of insecticidal activity as compared with DSM 2803. In particular, 4385 and 4353 show more selective activity against beetles than known coleopteran-active *B. thuringiensis* strains in that they are specifically larvacidal to Diabrotica spp.. In addition, strains JHCC 4835 and JHCC 4353 are larvacidal to lepidopteran pests whereas strain DSM 2803 is not. On the molecular level, the newly discovered gene in *Bacillus thuringiensis* strains JHCC 4835 and 4353 encode a gene product which shows a significantly different spectrum of insecticidal activity as compared with the coleopteran-specific endotoxin gene in DSM 2803 or the lepidopteran-specific CryIA endotoxin genes in HD1 and other var. *kurstaki* strains.

The new endotoxin gene encodes an 81.2 kilodalton endotoxin that has a completely novel activity spectrum: it is toxic to both lepidopteran and coleopteran larvae. This is particularly surprising since the *Bacillus thuringiensis* strain from which it is derived is not toxic to all Coleoptera, but rather is Diabrotica-specific. Possible explanations for this finding may include: a low concentration of this protein in the crystal that the microorganism produces; inaccessibility of the protein in the crystal; presence of the toxin in the crystal as a protoxin which is not converted to the active form in the gut of certain insects; or other so far unrecognised factors.

The *Bacillus thuringiensis* strains according to the invention may be prepared in any quantity required by fermenting a sample of NCIB 40091 or 40090 obtained from the National Collections of industrial and Marine Bacteria under suitable conditions in an appropriate medium. Such conditions and media are well known to the art. The media will, for example, generally contain a nitrogen source (eg fish protein) and a carbohydrate source such as starch. Suitable conditions include a temperature in the range 15–45° C., and an approximately neutral pH. Fermentation may be conveniently carried out in batches, typically for periods of 3–5 days.

E. coli strains carrying cloned endotoxin genes according to the invention may be prepared by growing cells to stationary phase on solid nutrient media (eg L agar) prior to scraping cell growth from the medium surface, lyophilising, and freezing before thawing and weighing out the insecticidal material.

Insecticidal compositions according to the invention may be obtained from the fermentation liquor by concentration, for example by centrifugation or filtration followed by addition of any desired and appropriate formulating agents. Formulating agents which may be useful include for example surface active agents, eg, wetting agents: solid diluents, dispersing agents and UV stabilisers. If desired, solid formulations may be prepared by known methods.

The process of the invention is generally carried out by treating (eg spraying) plants infested or liable to infestation by insects with insecticidal compositions as described above diluted with a diluent such as water. The insecticidal agent is the toxic δ-endotoxin: if desired this may be applied to the plants or insects infesting them independently of the bacteria that produce it. Separation of the crystalliferous protein from the bacteria *Bacillus thuringiensis*, or of the cloned gene product from the bacterium *E. coli*, is however generally not necessary.

Another method of carrying out the process of the invention is to arrange for the plant susceptible to insect attack to produce the δ-endotoxin in situ. This is done by cloning a δ-endotoxin gene from strain NCIB 40090 or NCIB 40091, by known means; providing it with a promoter sequence (for example the CaMV35S promoter) which will cause expression of the gene in plants; and transforming the plant by known methods. Suitable transformation methods may include the use of Ti plasmid vectors for Agrobacterium-mediated transformation of dicots, or direct DNA uptake methods such as embryo microinjection, or use of microprojectiles followed by protoplast regeneration. To obtain the greatest degree of expression of the gene the promoter sequence should be selected and engineered appropriately and other factors (for example codon usage) should be adapted to maximise expression in planta.

Coleopteran larvae which are combated by the process of the invention may be of various species. As noted above, the *Bacillus thuringiensis* strains of the invention kill only Diabrotica, including those shown in Table 5A below: while use of the insecticidal product from the cloned gene of our invention will kill other coleoptera as well.

TABLE 5A

| Common Name | Latin Name |
| --- | --- |
| Western Corn Rootworm | *Diabrotica virgifera virgifera* |
| Southern Corn Rootworm | *Diabrotica undecimpunctata howardi* |
| Northern Corn Rootworm | *Diabrotica barberi* |
| Mexican Corn Rootworm | *Diabrotica virgifera zea* |
| Banded Cucumber Beetle | *Diabrotica balteata* |
| Western Spotted Cucumber Beetle | *Diabrotica undecimpunctata undecimpunctata* |

Lepidopteran larvae which are combated by the process of the invention may include those listed in Table 5B.

TABLE 5B

| Tobacco budworm | *Heliothis virescens* |
| --- | --- |
| Corn earworm | *Heliothis zea* |
| European corn borer | *Ostrinia nubilalis* |
| Cabbage looper | *Trichoplusia ni* |
| Diamondback moth | *Plutella xylostella* |
| Fall army worm | *Spodoptera frugiperda* |
| Beat army worm | *Spodoptera exigua* |

The process of the invention may be used to protect a wide variety of plants prone to infestation by Coleoptera (Diabrotica, if the *Bacillus thuringiensis* strains are used) or Lepidoptera. Specific examples of commercially important plants to be protected by the invention are maize (corn), tomatoes, potatoes, cotton, tobacco and cucurbits.

*Bacillus thuringiensis* JHCC 4835 and 4353 are var. *kurstaki* strains according to tests with antibody to flagellar antigens. To date, var. *kurstaki* strains have been known only for their insecticidal effect on lepidopteran larvae. Surprisingly, these strains and indeed other *kurstaki* strains previously described by ICI (e.g. strain A20 deposited at the National Collections of Industrial and Marine Bacteria under accession number NCIB 12570 and the subject of our prior UK application no 8730132 filed Dec. 24 1987) are active against coleopteran larvae of the genus Diabrotica, in addition to their expected activity against Lepidoptera. Moreover if the 81 kD endotoxin gene is used as a hybridisation probe, strongly hybridising sequences can be found in both chromosomal and plasmid DNA samples from other known *Bacillus thuringiensis* strains. These strains include var. *kurstaki* strains such as HD1, HD73 and HD241, and the var. *kenyae* strain ED123. In spite of this, the 81 kD endotoxin gene of the present invention has not been previously described, or recognised as being present in these or other *Bacillus thuringiensis* strains.

BRIEF DESCRIPTION OF THE DRAWINGS

The invention may be further understood with reference to the accompanying drawings, in which:

FIGS. 5A–5U show the base sequence SEQ ID NO:1 the amino acid sequence SEQ ID NO:2, and the main restriction endonuclease recognition sites of the 81 kD endotoxin gene carried by pJH11;

DESCRIPTION OF THE INVENTION

Figure 1:
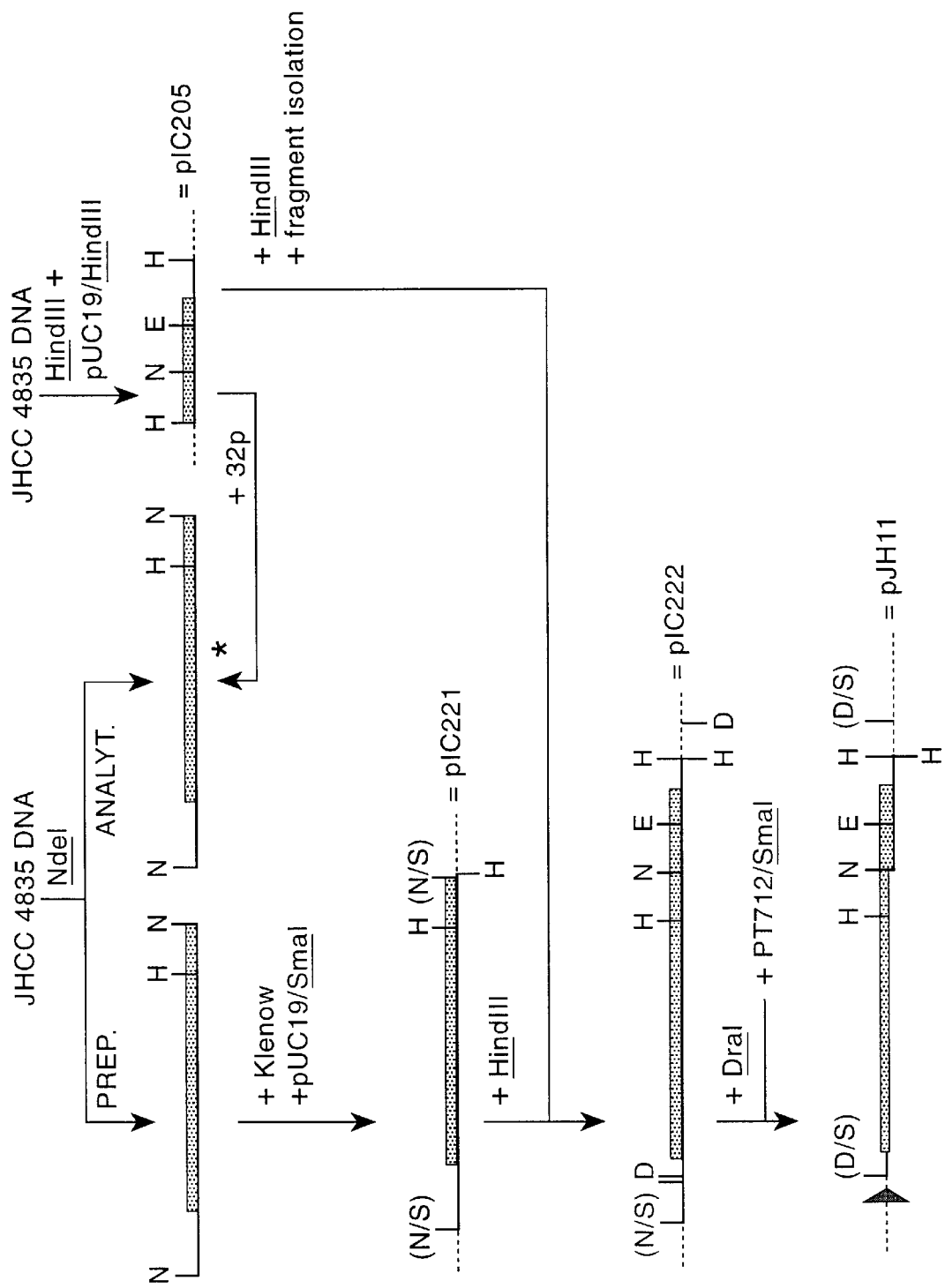
FIG. 1 shows diagrammatically the derivation of the cloned 81 kD endotoxin gene in the recombinant plasmid pJH11.

With further reference to FIG. 1, in this diagram, which is not drawn to scale, N represents restriction endonuclease NdeI, H=HindIII, E=EcoR1, D=DraI and S=SmaI. Restriction sites above the maps are in the cloned DNA, whereas sites below the maps are in the vector. Parentheses indicate sites rendered non-functional by "filling-in" with Klenow DNA polymerase. Dashed lines represent pUC19 vector DNA. Dotted lines represent PT712 vector DNA in clone pJH11 and the arrowhead represents the bacteriophage T7 promoter. The star represents a $^{32}$P-labelled DNA fragment.

Figure 2:
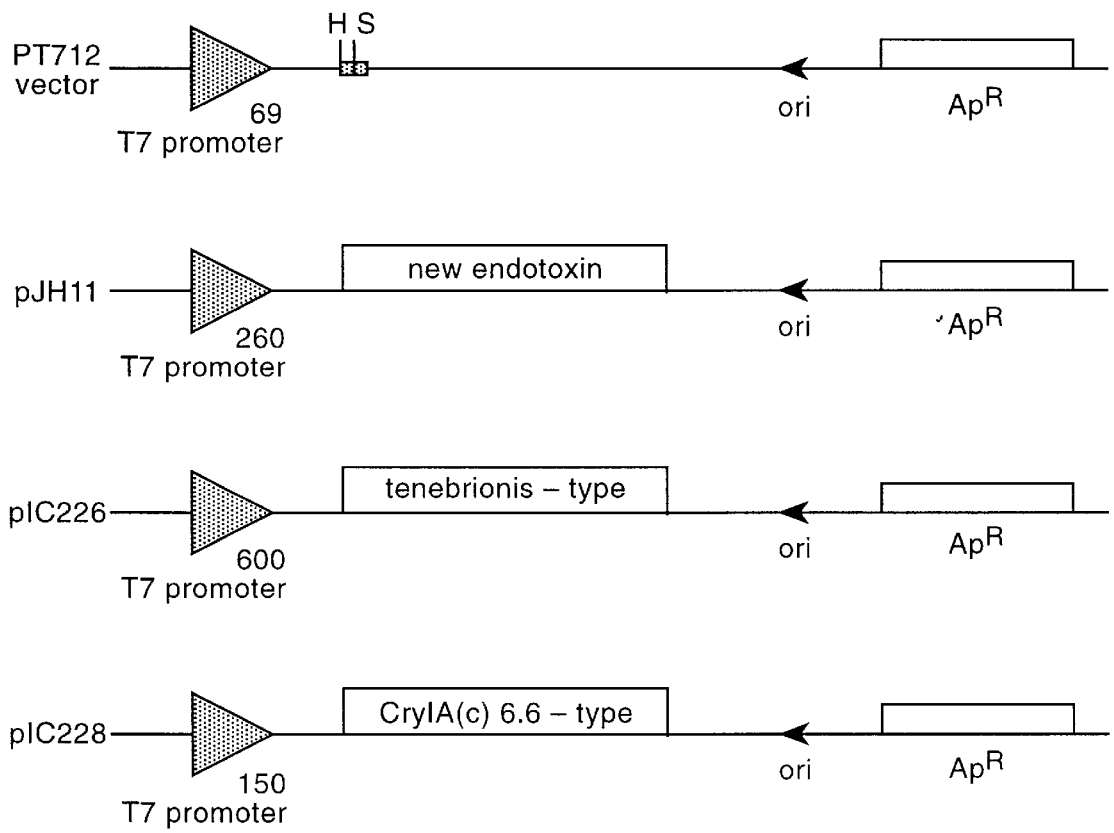
FIG. 2 shows diagrammatically the structure of pJH11, and the structures of the coleopteran-specific *tenebrionis*-type gene and the CryA 6.6-type gene cloned into the same vector system (PT712) and designated pIC 226 and pIC 228 respectively.

In FIG. 2, the figures below the maps represent the number of basepairs between the T7 RNA polymerase transcriptional start site and the beginning of the open reading frame. The large arrowhead represents the bacteriophage Y7 promoter. The solid block in PT712 represents the cloning site; H=HindIII and S=SmaI. Ap$^R$ indicates the gene encoding resistance to ampicillin.

Figure 3:
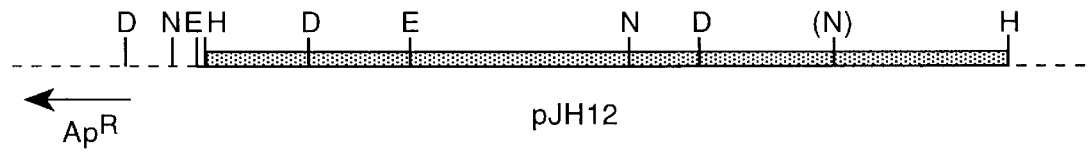
FIG. 3 shows diagrammatically the structure of the cloned lepidopteran-specific endotoxin gene in the recombinant plasmid pJH12.

In FIG. 3, the open box represents the cloned fragment which is about 7 kilobasepairs in length. The dashed lines indicate pUC19 vector DNA and Ap$^R$ is the gene encoding ampicillin resistance. The parentheses indicate an NdeI site which is only provisionally placed in the region shown; other restriction sites are represented by D=DraI, E=EcoR1, H=HindIII and N=NdeI.

Figure 4:
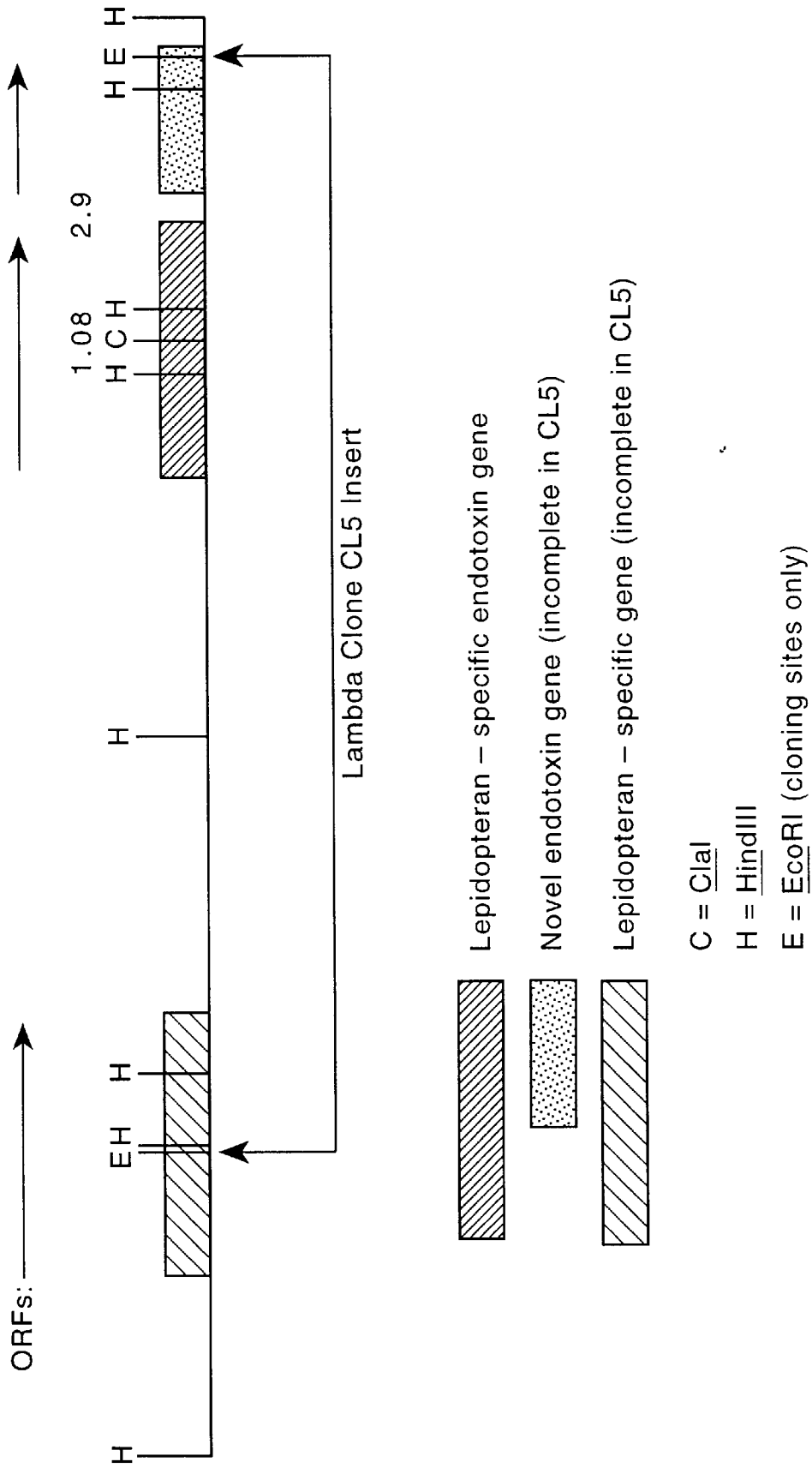
FIG. 4 shows diagrammatically the structure of the cloned lepidopteran-specific endotoxin gene in the recombinant lambda clone CL5.

With reference to FIG. 4, the only EcoR1 (E) sites shown are those at which the Lambda vector and the cloned insert fragment are joined. Open reading frames (ORFs) are shown by arrows above the map. The numbers above the map are the approximate fragment lengths of selected HindIII fragments. The ClaI (c) site shown is not the only ClaI site in the insert. The diagram is not drawn to scale; the cloned insert fragment is approximately 16 kilobase pairs in length.

FIGS. 5A–5U show the base sequence SEQ ID NO:1, the amino-acid sequence SEQ ID NO:2 and the main restriction sites of the gene encoding the 81 kD endotoxin protein and flanking DNA. The open reading frame begins at base number 355 and ends at base number 2514 with the G of the termination (Ter) codon TAG.

Figure 6:
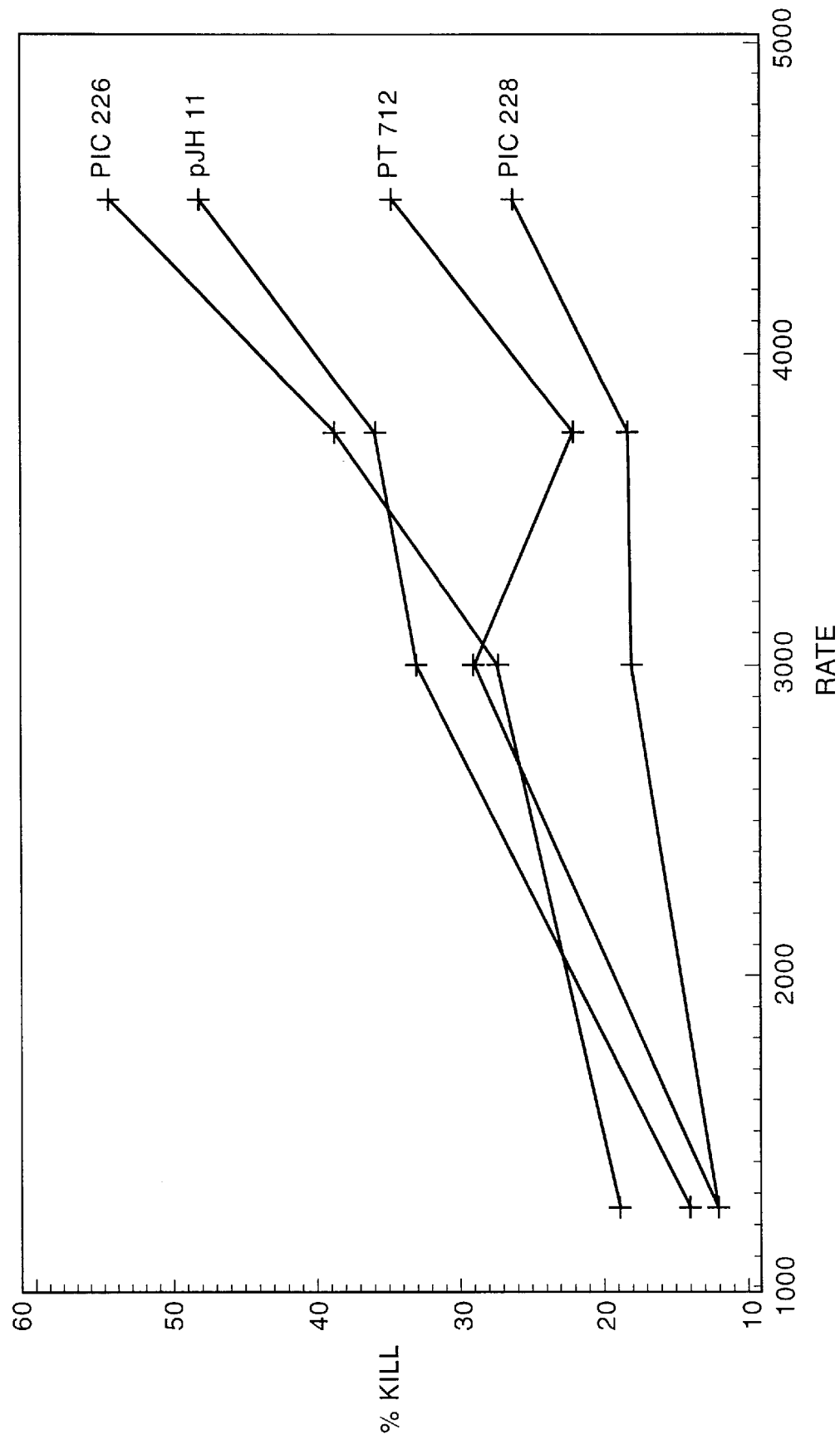
FIG. 6 shows graphically the mean values of 12 separate bioassays testing the efficacy of recombinant E. coli strain MC1022/pIC244 against first-instar larvae of Western Corn Rootworm at 4 days after treatment.

FIG. 6 is a graphical representation of the Western Corn Rootworm bioassay of cloned endotoxin gene products at 4 days after treatment (DAT). Points on the graph are mean values of percent mortality at a given rate.

Figure 7:
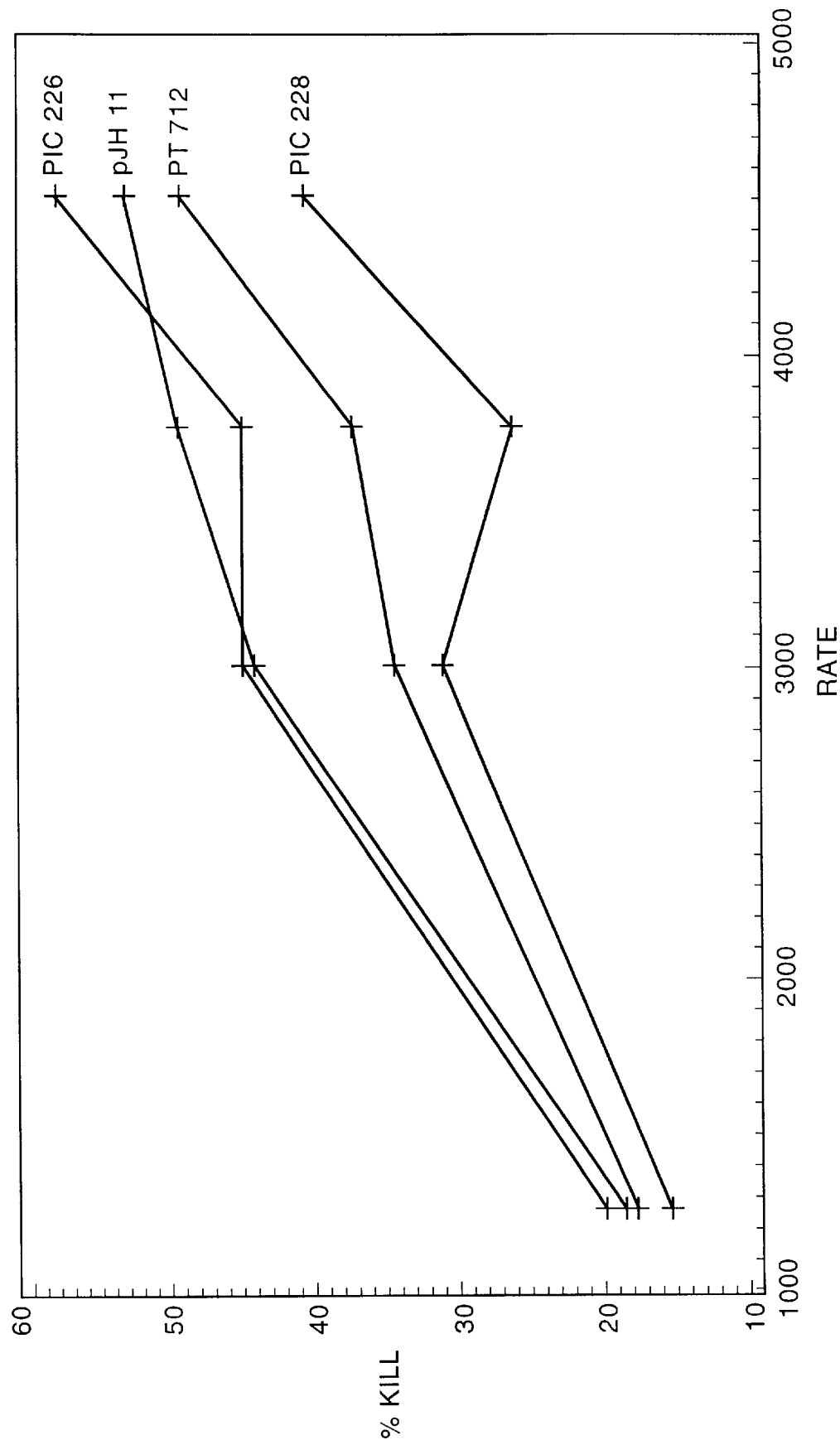
FIG. 7 shows graphically the mean values of 12 separate bioassays testing the efficacy of recombinant E. coli strain MC1022/pIC244 against first-instar larvae of Western Corn Rootworm at 5 days after treatment.

FIG. 7 is a graphical representation of the Western Corn Rootworm bioassay of cloned endotoxin gene products at 5 days after treatment (DAT). Points on the graph are mean values of percent mortality at a given rate.

The following Examples illustrate the invention,

EXAMPLE 1

Isolation of the B. thuringiensis strain JHCC 4835 according to the invention.

Soil samples were diluted by placing 5.0 g of the sample into 45 ml of 0.5% peptone to give a $10^{-1}$ dilution prior to emulsification. The sample was then heated to 60° C. for 10 minutes in a water bath. Sequential dilutions were then made prior to plating 0.1 ml of the $10^{-3}$ and $10^{-5}$ dilutions onto B. cereus selective agar plates (Bacillus cereus agar base, Oxoid) and esculin agar plates (in g/liter of $H_2O$: esculin 1.0; ferric citrate 0.5; peptone 10; NaCl 5; Oxoid agar 10). The plated samples were incubated at 30° C. for 5 days. Slides were made of potential B. thuringiensis colonies, stained according to Smirnoff's procedure and examined microscopically at 100×magnification for the presence of stained, parasporal crystals.

Crystal-positive colonies were streaked onto L agar (10 g tryptone, 10 g yeast extract, 5 g NaCl, 10 g agar per liter) in order to ensure a pure culture, and incubated at 30° C. Purified colonies were incubated overnight in L broth; after incubation an equal volume of 80% sterile glycerol was added prior to storage at −70° C.

The strain JHCC 4353 was extracted by a similar procedure.

EXAMPLE 2

Propagation of the B. thuringiensis Strains JHCC 4835 and JHCC 4353 on solid media.

Inoculum was transferred from a glycerol storage vial onto an L agar plate to check for purity. A representative sweep of colonies was then used to inoculate 5 ml of broth (10 g tryptone, 10 g yeast extract, 5 g NaCl per liter) prior to incubation with shaking at 30° C. for 3–5 hours. One milliliter of this culture was then used to inoculate a preparative (210 mm ×210 mm) Petri plate containing 300 ml of CRL 1 medium agar (in g or ml/liter of water: nutrient broth 8; glucose 6; yeast extract 5; xylose 0.5; cotton seed flour extract 30 ml; corn steep liquor 3.2 ml; Mary Mendel's salt mixture 1 ml; Oxoid agar 15). Mary Mendel's salt mixture is:

| Mary Mendel's Salts | |
|---|---|
| Distilled Water | 495 ml |
| HCl conc. | 5 ml |
| FeSO$_4$ | 2.5 g |
| MnSO$_4$, H$_2$O or MnCl$_2$.4H$_2$O | 0.98 g |
| ZnCl$_2$ or ZnSO$_4$.4.H$_2$O | 1.76 g |

Cultures were incubated for 5 days at 30° C. The cells, spores and crystals were then harvested by scraping confluent growth from the agar surface prior to freeze-drying.

EXAMPLE 3

Propagation of the B. thuringiensis strain JHCC 4835 and JHCC 4353 in liquid culture according to the invention.

Inoculum was transferred from a glycerol storage vial to a 250 ml Erylenmeyer flask containing 100 ml of CRL 1 medium (in g or ml/liter of water: nutrient broth 8; glucose 6; yeast extract 5; xylose 0.5; cotton seed flour extract 30 ml; corn steep liquor 3.2 ml; Mary Mendel's salt mixture 1 ml) and incubated with agitation at 30° C. and 3400 rpm. After 24 hours, the entire 100 ml was used to inoculate 1 liter of the same medium in a 2L flask; this was incubated with agitation for 5 days at 30° C. The cells, spores and crystals were then harvested by centrifugation and acetone precipitated using the Dulmage method.

EXAMPLE 4

Formulation according to the invention.

Upon completion of the fermentation cycle, JHCC 4353 or JHCC 4835 bacteria can be harvested by first separating the B. thuringiensis spores and crystals from the fermentation broth as described in Example 2. The recovered spores and crystals can be resuspended in 100 ml of water and formulated into a liquid concentrate by adding 4.9 g of Morwet D-425 (dispersing agent), 4.9 g of Veegum HV (suspending agent), 4.9 ml of Tween 80 (wetting agent) and 24.4 ml of Sorbo (anti-freezing agent). Each ingredient is added separately in order stated above. The product is kept at 40° C. prior to use.

EXAMPLE 5

Cloning of plasmid-derived endotoxin genes from B. thuringiensis strain 4835.

Endotoxin genes are cloned from covalently closed circular (ccc) plasmid DNA prepared from B. thuringiensis strain 4835 as follows:

A 500 ml culture of strain 4835 is grown in L broth at 37° C., with shaking, to an absorbance value at 600 mm of 1.00 optical density (O.D) units. Cells are harvested by centrifugation at 8000 revolutions per minute (rpm) for 10 minutes at 4° C., then re-suspended in 5 ml TE buffer (50 mM Tris HCl pH7.6, 20 mM EDTA). The resuspended cells are added to 95 ml TE buffer containing 1% sodium dodecyl sulphate (SDS) and 0.085M NaOH, pH2.4 lysin of the cell suspension occurs during a incubation at room temperature. 10 ml of 10% SDS are then added to the lysate; the solution is mixed gently prior to the gradual addition of 10 ml 2M Tris HCl pH7.0 with gentle mixing. 34 ml of 5M NaCl is added and the solution is mixed well prior to overnight incubation on ice-water. The lysate is centrifuged at 9000 rpm for 15 minutes at 4° C. and the supernatant carefully transferred to a new centrifuged bottle prior to the addition of 36 ml 50% polyethylene glycol (PEG) 600 in TE buffer. The lysate is incubated on ice-water for 3 hours (minimum) to overnight prior to centrifugation at 10,000 rpm for 10 minutes at 40° C. The pellet is dissolved in 9 ml TE buffer and 100 µl 5 mg/ml RNA (treated at 100° C. for 5 minutes, prior to use) and incubated at 45° C. for 10 minutes, prior to the addition of 9.23 g caesium chloride (CsCl). After the CsCl is dissolved, 0.9 ml of 5 mg/ml ethidium bromide is added prior to isopycnic centrifugation of the mixture at 40,000 rpm for 48 hours at 15° C., and isolation of the ccc DNA band. After removal of the CsCl and ethidium bromide by conventional techniques, high molecular weight plasmid ccc DNA (greater than 40 kilobase pairs) is isolated by size fractionation on 10%–40% sucrose step gradients prior to digestion with appropriate restriction endonucleases (ie, those which do not cleave the DNA in the endotoxin structural gene), ligation into appropriately digested plasmid cloning vectors (eg, pUC18 or pUC19), and transformation into an appropriate E. coli host strain (the specific strain used is MC1022, which is an ampicillin-sensitive strain of the genotype ara D139, Δ(ara, leu) 7697, Δ(lac Z) M15, gal U, gal K, str A. Transformants resistant to appropriate antibiotics which select for the introduced plasmid vector were then screened for recombinant endotoxin genes by standard DNA hybridization methods, using as probes the cloned tenebrionis gene (plus flanking sequences) and a cloned CryIA gene.

EXAMPLE 6

Cloning of chromosomal endotoxin genes from B. thuringiensis strain 4835.

Endotoxin genes were cloned from chromosomal DNA prepared from strain 4835 as follows:

A 500 ml culture of strain 4835 was grown in L-broth at 37° C., with shaking, to an Absorbance value at 600 nm of 1.00 optical density units. Cells were harvested by centrifugation at 8000 rounds per minute (rpm) for 10 minutes at 4° C., then re-suspended in 5 ml TES buffer (50 mM Tris-HCl pH7.5, 50 mM NaCl, 5 mM EDTA). Cells were treated for 30 minutes at 37° C. with lysozyme (0.5 mg/ml final concentration) and RNase (0.1 mg/ml final concentration taken from a stock solution of 5 mg/ml boiled at 100° C. for 5 minutes prior to use). Lysis was completed by the addition of Sarcosyl to give a final concentration of 0.8% and incubation at 37° C. for 60 minutes in the presence of Pronase (0.5 mg/ml final concentration taken from a stock solution of 5 mg/ml pre-incubated at 37° C. for 60 minutes prior to use). Lysate volume was adjusted to 9.0 ml in the 50 mM Tris-HCl pH 7.6, 10 mM EDTA, prior to the addition of 9.2 g caesium chloride (CsCl). After the CsCl dissolved, 1.25 ml of a 5 mg/ml solution of ethidium bromide was added prior to isopyonic centrifugation of the mixture at 40,000 rpm for 48 hours at 15° C.

After removal of CsCl and ethidium bromide by conventional techniques, an aliquot of purified chromosomal DNA was partially digested with the restriction endonuclease EcoR1 prior to ligation into EcoR1-digested bacteriophage λ EMBL4 vector DNA. Ligation reaction mixtures were packaged into viable phage particles using a commercially-available kit from Amersham international PLC.

The resultant recombinant phase particles were selected by growth on E. coli host strain PE392, a P2 lysogen of strain LE392 which has the genotype hsd R514 ($r_K^-, M_K^+$) sup E44, sup F58, lacY1 or Δ(lac2Y), gal K2, gal T22, met B1, trp R55. Recombinant phage carrying one or more endotoxin genes were detected by hybridisation of lysed plaques fixed to a duplicate set of nitrocellulose filters using as probes radiolabelled fragments of a CryIA-endotoxin gene and a 3'-terminal fragment of the gene for the 81 kD protein.

Plaques containing endotoxin genes were purified and characterised by restriction endonuclease mapping techniques well known in the art.

Chromosomal endotoxin genes can also be cloned directly into plasmid vectors (e.g. pUC19). This may necessitate cloning the gene in small fragments by the technique well known in the art as "chromosome walking". Problems with deletion events due to host-mediated homologous recombination can be circumvented by cloning in this manner and reconstructing the desired open reading frame by piecing the gene together after sequencing an appropriate number of overlapping gene fragments.

EXAMPLE 7

Solid media propagation of insecticidally-active *E. coli* strains carrying cloned endotoxin genes according to the invention.

Inoculum was transferred from a glycerol storage vial to L agar Petri plates containing antibiotics suitable for selection of the cloning vector. Inoculated plates were incubated 24–72 hours to allow for the appearance of characteristic colonial morphology. A selection of single colonies of the correct appearance (e.g. rough colonies in the case of *E. coli* strain BL21/pJH11 carrying the cloned the 81 kD endotoxin gene) was used to inoculate a small volume of L broth [15 g Tryptone, 7.5 g yeast extract, 7.5 g NaCl per 1500 ml total volume] containing an antibiotic (e.g. ampicillin) suitable for selection for the plasmid vector carrying the cloned endotoxin gene. Cultures were grown to an an Absorbance value at 600nm of 0.5–0.7 O.D. units. One milliliter (ml) of culture was used to inoculate, by spreading with a glass "spreader", a preparative (i.e. 245 mm×245 mm×20 mm) Petri plate containing L agar [L broth as above supplemented with 16 g Oxoid agar, an appropriate antibiotic and IPTG to a final concentration of 120 microgram/ml.]. Preparative plates were incubated overnight at 37° C. Bacterial growth was scraped from the preparative plates using a glass spreader. The scraped product, pooled from several plates if necessary, was transferred to a sterile plastic container and frozen for 2 hours at −20° C. prior to lyophilisation for 16–18 hours. The material was stored at −20° C. The dried product is crushed into an even powder prior to use as an insecticidal material in insect bioassays.

EXAMPLE 8

Purification of the novel 81.2 kilodalton endotoxin protein from the recombinant *E. coli* strain MC1022/pJH11. *E. coli* strain MC1022/pJH11 was prepared on solid media as described in Example 7, but the scraped cell mass was stored at −20° C. without lyophilisation. Frozen cells were thawed on ice prior to disruption by sonication at an amplitude of 14 microns for 9×20 seconds using a 1 cm diameter probe. The sonicated cells were then centrifuged at 9300×g at 4° C. to remove unbroken cells, prior to high-speed centrifugation (100,000×g for 60 minutes at 4° C.) to remove membranes. The high-speed extract was then subjected to ion-exchange chromatography over DEAE-Sepharose at pH 8.0. The column was then eluted with a 0–500 mM NaCl gradient, and fractions monitored by SDS-PAGE. Fractions containing the 81.2 kD protein were pooled, dialysed against 10 mM Tris pH8.0, and subjected to a second FPLC ion-exchange chromatography step, again eluting the bound proteins with a 0–500 mM NaCl gradient. Fractions containing the partially-purified 81.2 kD protein were identified and pooled prior to further purification by gel filtration chromatography. This process results in an endotoxin protein which is 90% pure and which may be used (with or without a concentration step) in insect bioassays.

Examples 9 and 10 illustrate the activity of the novel *B. thuringiensis* strains of the invention against different Diabrotica spp.

EXAMPLE 9

Efficacy of larvacidal activity of *B. thuringiensis* strain JHCC 4835 against Western Corn Rootworm (*Diabrotica virgifera virgifera*).

For each *B. thuringiensis* strain, a mixture of spores and crystals was prepared by incubating the organism at 30° C. for 5 days on 210 mm×210 mm Petri plates as in Example 2, scraping confluent growth from the agar surface and freeze drying. For tests on first instar larvae of Western Corn Rootworm (*Diabrotica virgifera virgifera*), freeze dried spores and crystals were mixed sterile water and a sterile sucrose solution to give the treatment rates indicated in Table 7 in parts per million (ppm) and a final sucrose concentration of 2.5%. The solubilised spore crystal (treatment) mixture was homogeneously dispersed by sonication in a water bath sonicator for 5 minutes. The treatment was then vortexed and applied as 0.075 ml of solution to a disk 1.5 cm in diameter cut from "Teri towels" (Kimberly Clark product #34770). One test consisted of 5 Teri towel disks with applied treatment, each placed in a separate plastic Falcon test dish prior to infestation with 5 first instar larvae per dish. Tests were placed in a closed styrofoam box with a moistened Teri towel as a humidity source; the box was incubated in a room held at 78° F.–80° F. for 3 or more days after treatment (DAT) prior to evaluation of the bioassay. The conditions inside the styrofoam box were 74° F.–76° F. and 80% relative humidity. Tests were evaluated using a dissecting microscope. The efficacy of these treatments at various concentrations (rates) is shown in Table 6.

EXAMPLE 10

Efficacy of larvacidal activity of *B. thuringiensis* strain JHCC 4835 against Southern Corn Rootworm (*Diabrotica undecimpunctata howardi*).

For each *B. thuringiensis* strain, a mixture of spores and crystals was prepared by incubating the organism at 30° C. for 5 days on 210 mm×210 mm Petri plates as in Example 2, scraping confluent growth from the agar surface and freeze drying. Tests on first instar Southern Corn Rootworm (*Diabrotica undecimpunctata howardi*) were set up, incubated and evaluated as described in Example 9. The efficacy of these treatments at various concentrations (rates) is shown in Table 8.

EXAMPLE 11

Specificity of insecticidal activity of *B. thuringiensis* strains JHCC 4835 and JHCC 4353.

A mixture of spores and crystals was prepared by incubating the organism at 30° C. for 5 days on 210 mm×210 mm Petrie plates as in Example 2, scraping confluent growth from the agar surface and freeze-drying. Freeze-dried spores and crystals were mixed with a sterile 2.5% sucrose solution for tests on first-instar Southern Corn Rootworm (*Diabrotica undecimpunctata howardi*) larvae. Freeze-dried spores and crystals were mixed with sterile H₂O and presented on potato leaves dipped in this suspension for tests on first-instar Colorado potato beetle (*Leptinotarsa decemlineata*) larvae. Freeze-dried spores and crystals were mixed with sterile H₂O and presented on cotton cotyledons dipped in this suspension for tests on Boll Weevil (*Anthonomus grandis*) adults. The efficacy of these preparations at various concentrations in parts per million (ppm) is shown in Table 8. Comparison of the activity spectrum *B. thuringiensis* variety *tenebrionis* (DSM 2803) with those of strains JHCC 4835 and JHCC 4353 shows the more selective effect of the latter two strains (Table 8).

The efficacy of *B. thuringiensis* strain JHCC 4835 in the control of various lepidopteran larvae is illustrated in Examples 12–15.

EXAMPLE 12

Efficacy of *B. thuringiensis* strain JHCC 4835 in the control of various lepidopteran larvae.

A mixture of spores and crystals was prepared as in Example 2, and mixed with an appropriate conventional artificial insect diet. Results are shown in Table 9 below. Comparison of the efficacy of *B. thuringiensis* variety *tenebrionis* (DSM 2803) with that of strain JHCC 4835 shows that only strain 4835, and the known var. *kurstaki* strain JHCC 4360, are insecticidal to lepidopteran larvae (Table 9).

EXAMPLE 13

Efficacy of *B. thuringiensis* strain JHCC 4835 in the control of Fall Army Worm (*Spodoptera frugiperda*).

A mixture of spores and crystals was prepared as in Example 2, and mixed with an appropriate conventional artificial insect diet. Results are shown in Table 10 below. Comparison of the efficacy of *B. thuringiensis* strain JHCC 4580 (an isolate very similar to var. *tenebrionis*) with that of strain JHCC 4835 shows that only strain 4835and the known *kurstaki* strain JHCC 4360, are insecticidal to *S. frugiperda* (Table 10).

EXAMPLE 14

Efficacy of *B. thuringiensis* strain JHCC 4835 in the control of Beet Army Worm (*Spodoptera exigua*).

A mixture of spores and crystals was prepared as in Example 2, and mixed with an appropriate conventional artificial insect diet. Comparison of the efficacy of *B. thuringiensis* strain JHCC 4580 (an isolate very similar to var. *tenebrionis* with that of strain JHCC 4835 shows that only strain 4835, and the known *kurstaki* strain JHCC 4360, are insecticidal to *S. exigua*.

EXAMPLE 15

Efficacy of *Bacillus thuringiensis* strains JHCC 4835 and 4353 in the control of *Heliothis viriscens*.

A mixture of spores and crystals was prepared as in Example 2, and mixed with an appropriate conventional artificial insect diet. Control of larvae obtained is shown in Table 12 below.

The efficacy and novel larvacidal activity spectrum of recombinant *E. coli* calls carrying the cloned endotoxin gene encoding the 81.2 kD protein are illustrated in Examples 16–18.

EXAMPLE 16

Efficacy of the larvacidal activity of the 81 kD endotoxin expressed by recombinant *E. coli* strain MC1022/pJH11 in controlling European Corn Borer (*Ostrinia nubilalis*).

*E. coli* strain MC1022/pJH11 was prepared on solid media as described in Example 7. Freeze-dried cells were thawed and mixed with an appropriate conventional artificial insect diet to give the final treatment concentration in parts per million (ppm) shown in Table 13. Tests were infested with first instar European corn borer larvae and evaluated at 6 days after treatment (DAT). *E. coli* strains carrying the recombinant plasmid with the 81 kD endotoxin gene (pJH11) and those carrying the CryIA 6.6 type lepidopteran-specific gene (pIC228) were insecticidal, whereas those carrying the vector only (PT712) or the *tenebrionis* -type gene (pIC226) were not.

EXAMPLE 17

Efficacy of the larvacidal activity of the 81 kD endotoxin expressed by recombinant *E. coli* strain MC1022/pJH11 in controlling Colorado Potato Beetle (*Leptinotarsa decemlineata*).

*E. coli* strain MC1022/pJH11 was prepared on solid media a described in Example 7. Freeze-dried cells were thawed, mixed with sterile H₂O and presented on potato leaves dipped in this suspension for tests on first-instar larvae of Colorado Potato Beetles (*Leptinotarsa decemlineata*) to give the final treatment concentration in parts per million (ppm) shown in Table 14. *E. coli* strains carrying the recombinant plasmid with the 81 kD endotoxin gene (pJH11) and those carrying the *tenebrionis* -type gene (pIC226) were insecticidal whereas those carrying the vector only (PT712) or the CryIA 6.6 type lepidopteran-specific gene (pIC228) were not.

EXAMPLE 18

Efficacy of the larvacidal activity of the 81 kD endotoxin expressed by recombinant *E. coli* strain MC1022/pJH11 in controlling Western Corn Rootworms (*Diabrotica virgifera virgifera*).

*E. coli* strain MC1022/pJH11 was prepared on solid media as described in Example 7. For tests on first instar larvae of Western Corn Rootworm (*Diabrotica virgifera virgifera*), freeze dried cells were thawed, mixed with sterile water and a sterile sucrose solution to give the treatment rates indicated and a final sucrose concentration of 2.5%. The solubilised cell (treatment) mixture was homogeneously dispersed by sonication in a water bath sonicator for 5 minutes. The treatment was then vortexed and applied as 0.075 ml of solution to a disk 1.5 cm in diameter cut from "Teri towels" (Kimberly Clark product #34770) as described in Example 9 to give the final treatment concentration in parts per million (ppm) shown in Tables 15 & 16. These tests were read at 4 and 5 DAT and the results were subjected to statistical analysis. Results are presented graphically in FIGS. 6 & 7 and indicate that *E. coli* strains carrying the recombinant plasmid with the the 81 kD endotoxin gene (pJH11) and those carrying the *tenebrionis* -type gene (pIC226) were insecticidal whereas those carrying the vector only (PT712) or the CryIA 6.6 type lepidopteran-specific gene (pIC228) were not; the differences in activity between these two groups of strains (pJH11 and pIC226 versus the vector PT712 and pIC228) are statistically significant.

The efficacy and novel larvacidal activity spectrum of the partially-purified and purified novel 81.2 kD endotoxin protein are illustrated in Examples 19–21.

EXAMPLE 19

Efficacy of the larvacidal activity of the partially-purified and purified 81 kD endotoxin in controlling European Corn Borer (*Ostrinia nubilalis*).

Partially-purified and purified 81 kD endotoxin protein was prepared from freeze-dried recombinant *E. coli* cells MC1022/pJH11 as described in Example 8. Fractions from the second FPLC ion-exchange column were designated MonoQ A, B, and C and contained about 50%, 50%, and 25% 81.2 kD endotoxin protein respectively. These fractions were added to conventional artificial insect diet to give the treatment rates in ppm shown in Table 17 in bioassays to test insecticidal activity on first-instar larvae of European corn borer (*Ostrinia nubilalis*). The results in Table 19 show that all fractions were active in producing either mortality or stunting of larval growth. Purified 81.2 kD protein was also tested and found to be insecticidal to European corn borer larvae and to stunt larval growth (Table 18).

EXAMPLE 20

Efficacy of the larvacidal activity of the partially-purified and purified 81 kD endotoxin in controlling Colorado Potato Beetle (*Leptinotarsa decemlineata*).

Partially-purified and purified 81.2 kD endotoxin protein was prepared from freeze-dried recombinant *E. coli* cells MC1022//pJH11 as described in Example 8. Fractions from the second, FPLC ion-exchange column were designated MonoQ A, B, and C and contained about 50%, 50%, and 25% 81.2 kD endotoxin protein respectively. These fractions and the purified 81.2 kD protein were mixed with sterile H$_2$O and presented on potato leaves dipped in this suspension for tests on first-instar larvae of Colorado Potato Beetles (*Leptinotarsa decemlineata*) to give the final treatment concentration in parts per million (ppm) shown in Table 19. The results in Table 19 show that all fractions were insecticidal to Colorado Potato Beetle larvae.

EXAMPLE 21

Efficacy of the larvacidal activity of the partially-purified and purified 81 kD endotoxin in controlling Western Corn Rootworms (*Diabrotica virgifera virgifera*).

Partially-purified and purified 81 kD novel endotoxin protein was prepared from freeze-dried recombinant *E. coli* cells MC1022/pJH11 as described in Example 8. Fractions from the second, FPLC ion-exchange column were designated MonoQ A, B, and C and contained about 50%, 50%, and 25% 81.2 kD endotoxin protein respectively. These fractions and the purified 81.2 kD protein were mixed with sterile water and a sterile sucrose solution to give the treatment rates indicated in Table 20, and a final sucrose concentration of 2.5%. Tests on first-instar larvae of Western Corn Rootworm were carried out as described in Example 18. The results in Table n indicate that the 81.2 kD endotoxin is insecticidal to Western Corn Rootworm larvae.

The following microorganisms and clones referred to in this specification have been deposited at the National Collections of industrial and Marine Bacteria, 23 St. Machar Drive, Aberdeen AB2 1RY, Scotland:

| Name | Deposit Number | Date |
| --- | --- | --- |
| *Bacillus thuringiensis* | | |
| A20 | 12570 | 20 October 1987 |
| JHCC 4835 | 40091 | 7 December 1988 |
| JHCC 4353 | 40090 | 7 December 1988 |
| *E. coli* | | |
| BL21/pJH11 | 40275 | 6 April 1990 |
| MC1022/pJH12 | 40278 | 24 April 1990 |
| Bacteriophage Lambda EMBL4 clone CL5 twr/se 01-May-1990 | 40279 | 26 April 1990 |

TABLE 1

MORPHOLOGY

| Strain | Crystals | Cell Morphology | Colony Morphology (Cultured on Bacillus Cereus selective Agar) |
| --- | --- | --- | --- |
| HD-1 | Medium bipyramids plus undefined shaped crystals | Rods with terminal spores which do not distend the cell | Large colonies, yellow centres. Egg yolk lecithinase: NEGATIVE |
| DMS 2803 | Small irregular crystals; few bipyrimidal crystals | Rods with terminal spores with do not distend the cell | Large Colonies, blue centres. Egg yolk lecithinase: NEGATIVE |
| JHCC 4353 | Large, mainly regular bipyrimidal crystals | Rods with oval, terminal or subterminal spores which do not distend the cell | Large blue colonies with yellow centres. Egg yolk lecithinase: POSITIVE |

TABLE 1-continued

MORPHOLOGY

| Strain | Crystals | Cell Morphology | Colony Morphology (Cultured on Bacillus Cereus selective Agar) |
|---|---|---|---|
| JHCC 4835 | Large, mainly regular bipyrimdal crystals | Rods with oval, terminal or subterminal spores which do not distend the cell | Large blue colonies with yellow centres. Egg yolk lecithinase: POSITIVE |

TABLE 2

Biochemical Markers on Microtitre Plate

| Reagent | HD-1 | DSM 2803 | JHCC 4353 | JHCC 4835 |
|---|---|---|---|---|
| Glycerol | − | − | − | − |
| Erythritol | − | − | − | − |
| D-arabinose | − | − | − | − |
| L-arabinose | − | − | − | − |
| Ribose | + | +/− | + | + |
| D-xylose | − | − | − | − |
| L-xylose | − | − | − | − |
| Adonitol | − | − | − | − |
| β-methyl-xyloside | − | − | − | − |
| Galactose | − | − | − | − |
| D-glucose | + | + | + | + |
| D-fructose | + | + | + | + |
| D-mannose | − | + | − | − |
| L-sorbose | − | − | − | − |
| Rhamnose | − | − | − | − |
| Dulcitol | − | − | − | − |
| Inositol | − | − | − | − |
| Mannitol | − | − | − | − |
| Sorbitol | − | − | − | − |
| α-methyl-D-mannoside | − | − | − | − |
| α-methyl-D-glucoside | − | − | − | − |
| N acetyl glucosamine | + | + | + | + |
| Amygdaline | − | − | − | − |
| Arbutine | + | + | + | + |
| Esculine | + | +/− | + | + |
| Salicine | + | − | + | + |
| Cellobiose | + | − | + | + |
| Maltose | + | + | + | + |
| Lactose | − | − | − | − |
| Melibiose | − | − | − | − |
| Saccharose | − | + | − | − |
| Trehalose | + | + | + | + |
| Inuline | − | − | − | − |
| Melezitose | − | − | − | − |
| D-raffinose | − | − | − | − |
| Amidon | + | + | + | + |
| Glycogene | + | + | + | + |
| Xylitol | − | − | − | − |
| β-gentiobiose | − | − | − | − |
| D-turanose | − | − | − | − |
| D-lyxose | − | − | − | − |
| D-tagatose | − | − | − | − |
| D-fucose | − | − | − | − |
| L-fucose | − | − | − | − |
| D-arabitol | − | − | − | − |
| L-arabitol | − | − | − | − |
| Gluconate | − | − | − | − |
| 2-ceto-glyconate | − | − | − | − |
| 5-ceto-gluconate | − | − | − | − |
| Ortho-nitro-phenyl galactoside (ONPG) | − | − | − | − |
| Arginine (ADC-arginine dihydrolase) | + | + | + | + |
| Lysine (LDH-lysine Decarboxylase) | + | − | − | − |
| Sodium Citrate (citrate utilisation) | − | + | + | + |
| Sodium Thiosulphate ($H_2S$ production) | − | − | − | − |
| Urea (urease) | + | − | + | + |
| Tryptophane (deaminase detection) | − | − | − | − |
| Tryptophane (indole production) | − | − | − | − |
| Sodium Pyruvate (VP) | + | + | + | + |
| Gelatine (Gelatinase) | + | + | + | + |
| $NO_3$—$NO_2$ Reduction | + | − | + | + |
| Ornithine decarboxylase (ODC) | − | − | − | − |

+ = Positive Reaction
− = Negative Reaction
+/− = Weak Reaction

TABLE 3

Biochemical Markers on ID-IDENT Plates

| Reagent | HD-1 | DSM 2803 | JHCC 4353 | JHCC 4835 |
|---|---|---|---|---|
| 2-naphthyl-phosphate | − | − | − | − |
| 2-naphthyl-butyrate | + | + | + | + |
| 2-naphthyl-caprylate | + | + | + | + |
| 2-naphthyl-myristate | + | + | + | + |
| L-leucyl-2-naphthylamide | + | + | + | + |
| L-valyl-2-naphthylamide | + | + | + | + |
| L-crystyl-2-naphthylamide | + | + | + | + |
| N-benzoyl-DL-arginine-2-naphthylamide | 0 | + | + | + |
| N-glutaryl-phenylalanine-2-naphthylamine | 0 | + | + | + |
| 2-naphthyl-phosphate | + | + | + | + |
| naphthol-AS-B1-phosphate | + | + | + | + |
| 6-bromo-2-naphthyl-αD-galactopyranoside | − | − | − | − |
| 2-naphthyl-βD-galactopyranoside | − | − | − | − |
| Naphtol-AS-B1-βD glucuronide | − | − | − | − |
| 2-naphthyl-αD-glucopyranoside | + | + | + | + |
| 6-bromo-2-naphthyl-βD-glucopyranoside | + | − | + | + |
| 1-naphthyl-N-acetyl-βD-glucosaminide | − | − | − | − |

TABLE 3-continued

| Biochemical Markers on ID-IDENT Plates | | | | |
|---|---|---|---|---|
| Reagent | HD-1 | DSM 2803 | JHCC 4353 | JHCC 4835 |
| 6-Bromo-2-naphthyl-αD-mannopyranoside | – | – | – | – |
| 2-naphthyl-αL-fucopyranoside | – | – | – | – |

ID-DENT is a Trade Mark of API Analytab Products

TABLE 7-continued

| | | *Diabrotica virgifera virgifera* % Mortality at 3 days after treatment | |
|---|---|---|---|
| Expt No | *B. thuringiensis* | Test Larvae* | Untreated Controls* |
| 2 | 4835 | 50 | 4 |
| | 4353 | 60 | 8 |

*25 first-instar larvae per test group

TABLE 4

SENSITIVITIES TO ANTIBIOTICS

| STRAIN | C | CT | F | SF | NA | ANP | S | TET | OA | K | VA | RIF | LI | CN | CR | CAR | E |
|---|---|---|---|---|---|---|---|---|---|---|---|---|---|---|---|---|---|
| HD-1 | S | R | S | S | S | R | S | S | S | S | S | S | S | S | S | S | S |
| DSM 2803 | S | R | S | R | S | R | S | S | S | R | S | S/R | S | S | S | R | S |
| JHCC 4353 | S | R | S | S | S | R | S | S | S | S | S | S | S | S | S | R | S |
| JHCC 4835 | S | R | S | S | S | R | S | S | S | S | S | S | S | S | S | R | S |

S = SENSITIVE R = RESISTANT S/R = REDUCED SENSITIVITY
C = Chloramphenicol 50 ug/ml
F = Nitrofuration 200 ug/ml
NA = Naladixic Acid 30 ug/ml
S = Streptomycin 25 ug/ml
TET = Tetracycline 50 ug/ml
VA = Vancomycin 30 ug/ml
OA = Oxolinic Acid 2 ug/ml
CN = Gentamicin 10 ug/ml
E = Erythromycin 10 ug/ml
CT = Colistin Sulphate 10 ug/ml
SF = Sulphfurazole 500 ug/ml
AMP = Ampicillin 25 ug/ul
CR = Cephaloridine 25 ug/ml
K = Kanamycin 30 ug/ml
RIF = Rifampicin 2 ug/ml
LI = Lincomycin 15 ug/ml
CAR = Carbenicillin 100 ug/ml

TABLE 6

| | | % Mortality | | | | | |
|---|---|---|---|---|---|---|---|
| Strain | ppm | SCRW 3 DAT | 6 DAT | ppm | CPB 3 DAT | ppm | BW 3 DAT |
| DSM 2803 | 4800 | 8 | 92 | 200 | 100 | 1200 | 87 |
| JHCC 4835 | 4800 | 38 | 92 | 200 | 7 | 1200 | 13 |
| JHCC 4353 | 4800 | 12 | 68 | 200 | 0 | 1200 | 13 |
| UNTREATED CONTROL | — | 0 | 4 | – | 0 | – | 20 | ppm = Parts per million
$CRW = Southern Corn Rootworm
CPB = Colorado Potato Beetle
BW = Boll Weevil
(RF) = % Reduction Feeding

TABLE 7

| | | *Diabrotica virgifera virgifera* % Mortality at 3 days after treatment | |
|---|---|---|---|
| Expt No | *B. thuringiensis* | Test Larvae* | Untreated Controls* |
| 1 | 4835 | 88 | 4 |
| | 4353 | 72 | 16 |

TABLE 8

| | Southern Corn Rootworm | | Boll Weevil | Colorado Potato Beetle |
|---|---|---|---|---|
| Bt Strain | 3 DAT 4800 ppm | 6 DAT 4800 ppm | 3 DAT 1200 ppm | 3 DAT 200 ppm |
| DSM 2803 *tenebrionis* | 8 | 92 | 87 | 100 |
| 4835 | 38 | 92 | 13 | 7 |
| 4353 | 12 | 68 | 13 | 0 |
| Control | 0 | 4 | 20 | 0 |

RESULTS = % MORTALITY
DAT = DAYS AFTER TREATMENT

TABLE 9

| Bt Strain | Rate (ppm) | *H.zea* | *T.ni* | *P.xylostella* |
|---|---|---|---|---|
| 4360 *kurstaki* | 5 | 85 | 95 | 100 |
| 4835 | 25 | 100 | 100 | 100 |
| | 250 | 100 | — | — |
| 4580 *tenebrionis* | 25 | 0 | 0 | 0 |

TABLE 9-continued

| Bt Strain | Rate (ppm) | H.zea | T.ni | P.xylostella |
|---|---|---|---|---|
| type | 250 | 5 | — | — |
| Control | — | 0 | 0 | 10 |

RESULTS = % MORTALITY AT 4 DAYS AFTER TREATMENT

TABLE 10

Bt SRAINS VERSUS *Spodoptera Frugiperda* AT 6 DAYS AFTER TREATMENT

| | 4580 tenebrionis | 4835 | 4360 kurstaki | Control |
|---|---|---|---|---|
| PREP 1 | 0 | 92 | 84 | 3 |
| PREP 2 | 0 | 60 | 80 | 3 |
| PREP 3 | 0 | 92 | 88 | 3 |
| PREP 4 | 8 | 100 | 100 | 3 |

RESULTS EXPRESSED AS % MORTALITY AT 80 PARTS PER MILLION

TABLE 12

B.t. STRAINS VERSUS *Heliothis virescens* AT 6 DAYS AFTER TREATMENT

| | 4580 tenebrionis | | 4835 | | 4360 kurstaki | |
|---|---|---|---|---|---|---|
| | 1 | 2 | 1 | 2 | 1 | 2 |
| PREP 1 | 4 | 8 | 100 | 96 | 100 | 100 |
| PREP 2 | 4 | 0 | 60 | 34 | 96 | 100 |
| PREP 3 | 9 | 0 | 100 | 100 | 100 | 100 |
| PREP 4 | 0 | 4 | 100 | 100 | 100 | 100 |

CONTROL 1 = 3.5%   CONTROL 2 = 2%
RESULTS EXPRESSED AS % MORTALITY AT 80 PARTS PER MILLION

TABLE 13

EUROPEAN CORN BORER BIOASSAYS

| 1ST Experiments | Prep Number | | | | | |
|---|---|---|---|---|---|---|
| Rate/% R.S. | 1 | 2 | 5 | 6 | 7 | 8 |
| pIC228 500 ppm | 30 | 30 | 63 | 5 | 10 | 75 |
| % R.S. | 100 | 100 | 100 | 100 | 100 | 100 |
| pJH11 500 ppm | 15 | 75 | 85 | 72 | 85 | 80 |
| % R.S. | 100 | 100 | 100 | 100 | 100 | 100 |
| pIC226 500 ppm | 0 | 0 | 10 | s | 0 | 10 |
| % R.S. | 0 | 0 | 11 | 6 | 0 | 3 |
| PT712 500 ppm | 0 | 0 | 10 | 0 | 0 | 0 |
| % R.S. | 0 | 0 | 17 | 5 | 0 | 0 |
| Control | 0 | 0 | 8 | 3 | 0 | 8 |
| % R.S. | 0 | 3 | 11 | 0 | 0 | 3 |
| 4835F2 10 ppm | — | — | 100 | 90 | 80 | 109 |
| % R.S. | — | — | xxx | 100 | 100 | xxx |

RESULTS = % MORTALITY AT 6 DAT
% R.S. = % SURVIVORS OF REDUCED SIZE

TABLE 14

COLORADO POTATO BEETLE BIOASSAYS

| | | PREP NUMBER | | | | | |
|---|---|---|---|---|---|---|---|
| SAMPLE | RATE | 1 | 2 | 5 | 6 | 7 | 8 |
| pIC226 | 5000 ppm | 84 | 84 | 60 | 53 | 27 | 93 |
| pJH11 | 5000 ppm | 84 | 100 | 60 | 93 | 79 | 87 |
| PT712 | 5000 ppm | 0 | 17 | 7 | 14 | 7 | 14 |
| pIC228 | 5000 ppm | 0 | 4 | 13 | 7 | 0 | 23 |
| Control | — | 0 | 0 | 7 | 7 | 0 | 13 |
| 4580F2 | 40 ppm | — | — | 100 | 93 | 100 | 73 |

RESULTS = % MORTALITY AT 3 DAYS AFTER TREATMENT

TABLE 15

WESTERN CORN ROOTWORM BIOASSAY

| E.coli Recombinant Plasmid | Rate (ppm) | Prep-Experiment | | | | | | |
|---|---|---|---|---|---|---|---|---|
| | | 5-1 | 5-2 | 6-1 | 6-2 | 7-1 | 7-2 | 8-1 | 8-2 |
| pIC226 (*tenebrionis*-type gene) | 4500 | 75 | 60 | 37 | 59 | 36 | 58 | 42 | 68 |
| | 3750 | 36 | 40 | 36 | 56 | 40 | 28 | 64 | 64 |
| | 3000 | 20 | 12 | 20 | 36 | 21 | 27 | 68 | 12 |
| | 1250 | — | 28 | 12 | 16 | 20 | 48 | 20 | 19 |
| pJH11 (novel gene) | 4500 | 16 | 52 | 60 | 56 | 36 | 44 | 64 | 58 |
| | 3750 | 28 | 36 | 42 | 13 | 46 | 40 | 68 | 48 |
| | 3000 | 08 | 12 | 36 | 46 | 52 | 44 | 36 | 29 |
| | 1250 | — | 12 | 20 | 04 | 40 | 0 | 16 | 28 |
| pIC228 (Cry IA lepidopteran-specific gene) | 4500 | 16 | 36 | 36 | 04 | 32 | 36 | 21 | 32 |
| | 3750 | 20 | 24 | 17 | 13 | 20 | 40 | 12 | 27 |
| | 3000 | 0 | 08 | 08 | 20 | 20 | 40 | 08 | 38 |
| | 1250 | — | 08 | 11 | 24 | 20 | 24 | 0 | 17 |
| PT712 (vector only) | 4500 | 18 | 24 | 40 | 24 | 52 | 14 | 42 | 64 |
| | 3750 | 08 | 28 | 36 | 40 | 32 | 24 | 12 | 28 |
| | 3000 | 12 | 36 | 12 | 32 | 36 | 28 | 48 | 28 |
| | 1250 | — | 12 | 12 | 16 | 24 | 04 | 20 | 16 |

RESULTS = % MORTALITY AT 4 DAYS AFTER TREATMENT

TABLE 16

WESTERN CORN ROOTWORM BIOASSAY

| E.coli Recombinant Plasmid | Rate (ppm) | Prep-Experiment | | | | | | |
|---|---|---|---|---|---|---|---|---|
| | | 5-1 | 5-2 | 6-1 | 6-2 | 7-1 | 7-2 | 8-1 | 8-2 |
| pIC226 (*tenebrionis*-type gene) | 4500 | 75 | 60 | 37 | 59 | 36 | 58 | 42 | 68 |
| | 3750 | 36 | 40 | 36 | 56 | 40 | 28 | 64 | 64 |
| | 3000 | 68 | 44 | 56 | 40 | 36 | 48 | 100 | 44 |
| | 1250 | — | 28 | 20 | 28 | 44 | 56 | 37 | 29 |
| pJH11 (novel gene) | 4500 | 56 | 56 | 88 | 68 | 68 | 76 | 84 | 67 |
| | 3750 | 52 | 72 | 92 | 28 | 73 | 88 | 92 | 75 |
| | 3000 | 12 | 40 | 79 | 56 | 77 | 64 | 60 | 68 |
| | 1250 | — | 32 | 24 | 20 | 52 | 04 | 32 | 24 |
| pIC228 (Cry IA lepidopteran-specific gene) | 4500 | 27 | 60 | 64 | 44 | 64 | 54 | 54 | 54 |
| | 3750 | 32 | 40 | 25 | 52 | 32 | 48 | 29 | 50 |
| | 3000 | 04 | 44 | 36 | 60 | 44 | 44 | 07 | 12 |
| | 1250 | — | 24 | 15 | 40 | 20 | 40 | 07 | 29 |
| PT712 (vector only) | 4500 | 40 | 36 | 76 | 40 | 68 | 68 | 79 | 96 |
| | 3750 | 40 | 56 | 60 | 44 | 56 | 52 | 30 | 72 |
| | 3000 | 24 | 52 | 40 | 40 | 42 | 36 | 64 | 56 |
| | 1250 | — | 20 | 13 | 32 | 36 | 13 | 41 | 24 |

RESULTS = MORTALITY AT 5 DAYS AFTER TREATMENT

TABLE 17

EUROPEAN CORN BORER BIOASSAY AT 6 DAYS TREATMENT

| Rate (ppm) | Prep | NON-TREATMENT CONTROLS Pre | NON-TREATMENT CONTROLS Post | (% MORTALITY/AVE. SIZE IN mm) MonoQ Fractions A | B | C | B.t. Strain 4835 |
|---|---|---|---|---|---|---|---|
| 115 | 1 | — | — | 88/1.5 | | | |
| 98 | 2 | | | | | 56/1.75 | |
| 67 | 1 | | | | | 66/1.5 | |
| 65 | 2 | | | | | 67/1.8 | |
| 65 | 3 | | | | | 78/1.5 | |
| 62 | 1 | | | | 100/1.1 | | |
| 57 | 2 | | | | 71/2.0 | | |
| 42 | 2 | | | 89/1.5 | | | |
| 11.5 | 3 | | | | | | 78/1.75 |
| 10 | 2 | | | | | | 62/1.8 |
| 6.5 | 2 | | | | | 17/2.7 | |
| 6.5 | 3 | | | | | 22/3.1 | |
| 6.3 | 1 | | | | | 22/2.7 | |
| 6.0 | 2 | | | | | 20/2.5 | |
| 4 | 2 | | | 0/2.4 | | | |
| 3.8 | 1 | | | 11/5.4 | | | |
| 3 | 1 | | | | | 0/5.0 | |
| — | 1 | 0/8.5 | 0/10 | | | | |
| — | 2 | 11/6.2 | 0/6.0 | | | | |
| — | 3 | 0/9.5 | 13/9.1 | | | | |

AVE SIZE IN mm = Average Size Of Surviving Larvae

TABLE 18

81kD PROTEIN VS. EUROPEAN CORN BORER

| | | | IA | JH | |
|---|---|---|---|---|---|
| | | Rate | % Mortality | % Mortality | Ave. Size |
| PREP 1 | | | | | |
| 81kD | Prot | 83 ppm | — | 0 | 2.7 mm |
| 17/20 | Ctrl | 5 ppm | — | 0 | 9.5 mm |
| Tris | Ctrl | — | — | 0 | 10 mm |
| PREP 2 | | | | | |
| 81kD | Prot | 16 ppm | 100 | — | — |
| | | 9.5 ppm | — | 25 | 2.1 mm |
| 17/20 | Ctrl | 5 ppm | — | 0 | 6 mm |
| Tril | Ctrl | — | — | 40 | 0 | 6 mm |

IA = IOWA, JH = JEALOTT'S HILL, CTRL = CONTROL
AVE SIZE = AVERAGE SIZE OF SURVIVING LARVAE

TABLE 19

81kD PROTEIN VERSUS COLORADO POTATO BEETLE

| | | Mono Q Fractions | | | | B.t. Strain |
|---|---|---|---|---|---|---|
| | Control | A | B | C | 81kD | 4580 |
| PREP 1 | | | | | | |
| Rate (ppm): | — | 330 | 213 | 270 | — | 40 |
| | 0 | 47 | 21 | 47 | — | 80 |
| PREP 2 | | | | | | |
| Rate (ppm): | — | 466 | 366 | 342 | 148 | 40 |
| | 0 | 87 | 67 | 87 | 33 | 100 |
| PREP 3 | | | | | | |
| Rate (ppm): | — | — | — | 588 | 257 | 40 |
| | 0 | — | — | 60 | 73 | 80 |

Results = % Mortality at 3 Days After Treatment

TABLE 20

B1 kD PROTEIN VERSUS WESTERN CORN ROOTWORM

| | | % Mortality at; | |
|---|---|---|---|
| Sample | Rate | 3 DAT | 4 DAT |
| 81kD Protein | 900 ppm | 98 | 100 |
| Tris Control | — | 0 | 0 |
| Control (2) | — | 0 | 0 |

DAT = DAYS AFTER TREATMENT

We claim:

1. Strains JHCC 4835 and JHCC 4353 of *Bacillus thuringiensis*, deposited at the National Collection of Industrial and Marine Bacteria (NCIMB) in Scotland under accession numbers NCIMB 40091 and NCIMB 40090, respectively.

2. An insecticidal composition containing said *B. thuringiensis* strain JHCC 4835 (NCIMB 40091) according to claim 1.

3. An insecticidal composition containing said *B. thuringiensis* strain JHCC 4353 (NCIMB 40090) according to claim 1.

4. A recombinant DNA comprised of an insecticidal endotoxin gene encoded by a clone selected from the group consisting of pJH11, pJH12, and CL5, deposited at the National Collection of Industrial and Marine Bacteria (NCIMB) in Scotland under accession numbers NCIMB 40275, NCIMB 40278, and NCIMB 40279, respectively.

5. A recombinant DNA comprised of an insecticidal endotoxin gene encoding an amino acid sequence from amino acid position 119 to amino acid position 837 of SEQ ID NO:2.

6. The recombinant DNA according to claim 5, wherein said insecticidal endotoxin gene has a nucleotide sequence from nucleotide position 355 to nucleotide position 2511 of SEQ ID NO:1.

7. The recombinant DNA according to claim 5 or 6, wherein said amino acid sequence encodes a protein having a molecular weight of about 81.2 kilodaltons.

8. A process for protecting plants against attack by susceptible insects of the order Coleoptera or Lepidoptera which comprises transforming plant material with said recombinant DNA according to one of claims 4–6 and regenerating said transformed material into a plant which expresses said insecticidal endotoxin gene.

9. The process according to claim 8, wherein said plant is selected from the group consisting of maize (corn), potato, tomato, cotton, tobacco, and cucurbit.

10. The process according to claim 8, wherein said plant which expresses said insecticidal endotoxin gene is an insect selected from the group consisting of Western corn rootworm, Northern corn rootworm, Southern corn rootworm, European corn borer, and corn earworm.

11. A plant transformed with said recombinant DNA according to one of claims 4–6.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 2965 base pairs
        (B) TYPE: nucleic acid
        (C) STRANDEDNESS: both (D) TOPOLOGY: linear (xi) SEQUENCE DESCRIPTION: SEQ ID NO:1:

```
CATATGTATA GAGCAACTTA ATCAAGCAGA GATATTTTCA CCTATCGATG AAAATATCTC      60
TGCTTTTTCT TTTTTTATTT GGTATATGCT TTACTTGTAA TCGAAAATAA AGCACTAATA     120
AGAGTATTTA TAGGTGTTTG AAGTTATTTC AGTTCATTTT TAAAGAAGGT TTAAAGACGT     180
TAGAAAGTTA TTAAGGAATA ATATTTATTA GTAAATTCCA CATATATTAT ATAATTAATT     240
ATGAAATATA TGTATAAATT GAAAATGCTT TATTTGACAT TACAGCTAAG TATAATTTTG     300
TATGAATAAA ATTATATCTG AAAATTAAAT AATAGTATAA GTGGAGGGAT TAATATGAAA     360
CTAAAGAATC AAGATAAGCA TCAAAGTTTT TCTAGCAATG CGAAAGTAGA TAAAATCTCT     420
ACGGATTCAC TAAAAAATGA AACAGATATA GAATTACAAA ACATTAATCA TGAAGATTGT     480
TTGAAAATGT CTGAGTATGA AAATGTAGAG CCGTTTGTTA GTGCATCAAC AATTCAAACA     540
GGTATTGGTA TTGCGGGTAA AATACTTGGT ACCCTAGGCG TTCCTTTTGC AGGACAAGTA     600
GCTAGTCTTT ATAGTTTTAT CTTAGGTGAG CTATGGCCTA AGGGGAAAAA TCAATGGGAA     660
ATCTTTATGG AACATGTAGA AGAGATTATT AATCAAAAAA TATCAACTTA TGCAAGAAAT     720
AAAGCACTTA CAGACTTGAA AGGATTAGGA GATGCCTTAG CTGTCTACCA TGATTCGCTT     780
GAAAGTTGGG TTGGAAATCG TAATAACACA AGGGCTAGGA GTGTTGTCAA GAGCCAATAT     840
ATCGCATTAG AATTGATGTT CGTTCAGAAA CTACCTTCTT TTGCAGTGTC TGGAGAGGAG     900
GTACCATTAT TACCGATATA TGCCCAAGCT GCAAATTTAC ATTTGTTGCT ATTAAGAGAT     960
GCATCTATTT TTGGAAAAGA GTGGGGATTA TCATCTTCAG AAATTTCAAC ATTTTATAAC    1020
CGTCAAGTCG AACGAGCAGG AGATTATTCC TACCATTGTG TGAAATGGTA TAGCACAGGT    1080
CTAAATAACT TGAGGGGTAC AAATGCCGAA AGTTGGGTAC GATATAATCA ATTCCGTAGA    1140
GACATGACTT AATGGTACT AGATTAGTG GCACTATTTC CAAGCTATGA TACACAAATG    1200
TATCCAATTA AAACTACAGC CCAACTTACA AGAGAAGTAT ATACAGACGC AATTGGGACA    1260
GTACATCCGC ATCCAAGTTT TACAAGTACG ACTTGGTATA ATAATAATGC ACCTTCGTTC    1320
TCTGCCATAG AGGCTGCTGT TGTTCGAAAC CCGCATCTAC TCGATTTTCT AGAACAAGTT    1380
ACAATTTACA GCTTATTAAG TCGATGGAGT AACACTCAGT ATATGAATAT GTGGGGAGGA    1440
CATAAACTAG AATTCCGAAC AATAGGAGGA ACGTTAAATA TCTCAACACA AGGATCTACT    1500
AATACTTCTA TTAATCCTGT AACATTACCG TTCACTTCTC GAGACGTCTA TAGGACTGAA    1560
TCATTGGCAG GGCTGAATCT ATTTTTAACT CAACCTGTTA ATGGAGTACC TAGGGTTGAT    1620
TTTCATTGGA AATTCGTCAC ACATCCGATC GCATCTGATA ATTTCTATTA TCCAGGGTAT    1680
GCTGGAATTG GGACGCAATT ACAGGATTCA GAAAATGAAT TACCACCTGA AGCAACAGGA    1740
CAGCCAAATT ATGAATCTTA TAGTCATAGA TTATCTCATA TAGGACTCAT TTCAGCATCA    1800
CATGTGAAAG CATTGGTATA TTCTTGGACG CATCGTAGTG CAGATCGTAC AAATACAATT    1860
GAGCCAAATA GCATTACACA AATACCATTA GTAAAAGCTT TCAATCTGTC TTCAGGTGCC    1920
GCTGTAGTGA GAGGACCAGG ATTTACAGGT GGGGATATCC TTCGAAGAAC GAATACTGGT    1980
ACATTTGGGG ATATACGAGT AAATATTAAT CCACCATTTG CACAAAGATA TCGCGTGAGG    2040
ATTCGCTATG CTTCTACCAC AGATTACAA TTCCATACGT CAATTAACGG TAAAGCTATT    2100
AATCAAGGTA ATTTTTCAGC AACTATGAAT AGAGGAGAGG ACTTAGACTA TAAAACCTTT    2160
MGAACTGTAG GCTTTACCAC TCCATTTAGC TTTTTAGATG TACAAAGTAC ATTCACAATA    2220
GGTGCTTGGA ACTTCTCTTC AGGTAACGAA GTTTATATAG ATAGAATTGA ATTTGTTCCG    2280
```

```
GTAGAAGTAA CATATGAGGC AGAATATGAT TTTGAAAAAG CGCAAGAGAA GGTTACTGCA      2340

CTGTTTACAT CTACGAATCC AAGAGGATTA AAAACAGATG TAAAGGATTA TCATATTGAC      2400

CAGGTATCAA ATTTAGTAGA GTCTCTATCA GATGAATTCT ATCTTGATGA AAAGAGAGAA      2460

TTATTCGAGA TAGTTAAATA CGCGAAGCAA CTCCATATTG AGCGTAACAT GTAGAATTAA      2520

AATCTACCTA AATCCAGAAA AATAAAAGGG TTAAATATAC AATTCTTGTA CCAATATTTT      2580

GAGTGATTAG ATGTAGGATG AAATTTAATT GTATGCTATT TAACAGTAGA GATATTAAAA      2640

ATTAATTTAT CTATACATTA ATAGTATAGA CATACAAACA TAAGAGAGCA TTGTCTTTTC      2700

GTAGGCTACA ATGCTCTCTA TTTACTATTT ATTTTTCTTT TGTATCTTCA AATTGACGTT      2760

GTTCTAAGCG TTCTATTGCA GCTCGTCGTT TAGTATCATC AATGTTTGTA TAAAGAGATG      2820

TTGTTTCCAT AGAATTATGT CCCATTTGAT TTGCTAATAA TACTAAATCT TTATTTTCAT      2880

TATAGTGATT AGTAGCATAA GTATGACGTA ATTTATGAGG GCTTTTCTTT TCATCAAAAG      2940

CCCTTGTGTA TTTCTCTGTA AGCTT                                            2965
```

(2) INFORMATION FOR SEQ ID NO:2:

(i) SEQUENCE CHARACTERISTICS:
        (A) LENGTH: 2965 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: CDS
        (B) LOCATION: 1..2965

(xi) SEQUENCE DESCRIPTION: SEQ ID NO:2:

```
CAT ATG TAT AGA GCA ACT TAA TCA AGC AGA GAT ATT TTC ACC TAT CGA          48
His Met Tyr Arg Ala Thr  *  Ser Ser Arg Asp Ile Phe Thr Tyr Arg
 1           5                  10                  15

TGA AAA TAT CTC TGC TTT TTC TTT TTT TAT TTG GTA TAT GCT TTA CTT          96
 *  Lys Tyr Leu Cys Phe Phe Phe Phe Tyr Leu Val Tyr Ala Leu Leu
             20                  25                  30

GTA ATC GAA AAT AAA GCA CTA ATA AGA GTA TTT ATA GGT GTT TGA AGT         144
Val Ile Glu Asn Lys Ala Leu Ile Arg Val Phe Ile Gly Val  *  Ser
         35                  40                  45

TAT TTC AGT TCA TTT TTA AAG AAG GTT TAA AGA CGT TAG AAA GTT ATT         192
Tyr Phe Ser Ser Phe Leu Lys Lys Val  *  Arg Arg  *  Lys Val Ile
     50                  55                  60

AAG GAA TAA TAT TTA TTA GTA AAT TCC ACA TAT ATT ATA TAA TTA ATT         240
Lys Glu  *  Tyr Leu Leu Val Asn Ser Thr Tyr Ile Ile  *  Leu Ile
 65              70                  75                  80

ATG AAA TAT ATG TAT AAA TTG AAA ATG CTT TAT TTG ACA TTA CAG CTA         288
Met Lys Tyr Met Tyr Lys Leu Lys Met Leu Tyr Leu Thr Leu Gln Leu
             85                  90                  95

AGT ATA ATT TTG TAT GAA TAA AAT TAT ATC TGA AAA TTA AAT AAT AGT         336
Ser Ile Ile Leu Tyr Glu  *  Asn Tyr Ile  *  Lys Leu Asn Asn Ser
            100                 105                 110

ATA AGT GGA GGG ATT AAT ATG AAA CTA AAG AAT CAA GAT AAG CAT CAA         384
Ile Ser Gly Gly Ile Asn Met Lys Leu Lys Asn Gln Asp Lys His Gln
        115                 120                 125

AGT TTT TCT AGC AAT GCG AAA GTA GAT AAA ATC TCT ACG GAT TCA CTA         432
Ser Phe Ser Ser Asn Ala Lys Val Asp Lys Ile Ser Thr Asp Ser Leu
    130                 135                 140

AAA AAT GAA ACA GAT ATA GAA TTA CAA AAC ATT AAT CAT GAA GAT TGT         480
Lys Asn Glu Thr Asp Ile Glu Leu Gln Asn Ile Asn His Glu Asp Cys
```

```
                145                 150                 155                 160

TTG AAA ATG TCT GAG TAT GAA AAT GTA GAG CCG TTT GTT AGT GCA TCA              528
Leu Lys Met Ser Glu Tyr Glu Asn Val Glu Pro Phe Val Ser Ala Ser
                165                 170                 175

ACA ATT CAA ACA GGT ATT GGT ATT GCG GGT AAA ATA CTT GGT ACC CTA              576
Thr Ile Gln Thr Gly Ile Gly Ile Ala Gly Lys Ile Leu Gly Thr Leu
                180                 185                 190

GGC GTT CCT TTT GCA GGA CAA GTA GCT AGT CTT TAT AGT TTT ATC TTA              624
Gly Val Pro Phe Ala Gly Gln Val Ala Ser Leu Tyr Ser Phe Ile Leu
                195                 200                 205

GGT GAG CTA TGG CCT AAG GGG AAA AAT CAA TGG GAA ATC TTT ATG GAA              672
Gly Glu Leu Trp Pro Lys Gly Lys Asn Gln Trp Glu Ile Phe Met Glu
                210                 215                 220

CAT GTA GAA GAG ATT ATT AAT CAA AAA ATA TCA ACT TAT GCA AGA AAT              720
His Val Glu Glu Ile Ile Asn Gln Lys Ile Ser Thr Tyr Ala Arg Asn
225                 230                 235                 240

AAA GCA CTT ACA GAC TTG AAA GGA TTA GGA GAT GCC TTA GCT GTC TAC              768
Lys Ala Leu Thr Asp Leu Lys Gly Leu Gly Asp Ala Leu Ala Val Tyr
                245                 250                 255

CAT GAT TCG CTT GAA AGT TGG GTT GGA AAT CGT AAT AAC ACA AGG GCT              816
His Asp Ser Leu Glu Ser Trp Val Gly Asn Arg Asn Asn Thr Arg Ala
                260                 265                 270

AGG AGT GTT GTC AAG AGC CAA TAT ATC GCA TTA GAA TTG ATG TTC GTT              864
Arg Ser Val Val Lys Ser Gln Tyr Ile Ala Leu Glu Leu Met Phe Val
                275                 280                 285

CAG AAA CTA CCT TCT TTT GCA GTG TCT GGA GAG GAG GTA CCA TTA TTA              912
Gln Lys Leu Pro Ser Phe Ala Val Ser Gly Glu Glu Val Pro Leu Leu
                290                 295                 300

CCG ATA TAT GCC CAA GCT GCA AAT TTA CAT TTG TTG CTA TTA AGA GAT              960
Pro Ile Tyr Ala Gln Ala Ala Asn Leu His Leu Leu Leu Leu Arg Asp
305                 310                 315                 320

GCA TCT ATT TTT GGA AAA GAG TGG GGA TTA TCA TCT TCA GAA ATT TCA             1008
Ala Ser Ile Phe Gly Lys Glu Trp Gly Leu Ser Ser Ser Glu Ile Ser
                325                 330                 335

ACA TTT TAT AAC CGT CAA GTC GAA CGA GCA GGA GAT TAT TCC TAC CAT             1056
Thr Phe Tyr Asn Arg Gln Val Glu Arg Ala Gly Asp Tyr Ser Tyr His
                340                 345                 350

TGT GTG AAA TGG TAT AGC ACA GGT CTA AAT AAC TTG AGG GGT ACA AAT             1104
Cys Val Lys Trp Tyr Ser Thr Gly Leu Asn Asn Leu Arg Gly Thr Asn
                355                 360                 365

GCC GAA AGT TGG GTA CGA TAT AAT CAA TTC CGT AGA GAC ATG ACT TTA             1152
Ala Glu Ser Trp Val Arg Tyr Asn Gln Phe Arg Arg Asp Met Thr Leu
                370                 375                 380

ATG GTA CTA GAT TTA GTG GCA CTA TTT CCA AGC TAT GAT ACA CAA ATG             1200
Met Val Leu Asp Leu Val Ala Leu Phe Pro Ser Tyr Asp Thr Gln Met
385                 390                 395                 400

TAT CCA ATT AAA ACT ACA GCC CAA CTT ACA AGA GAA GTA TAT ACA GAC             1248
Tyr Pro Ile Lys Thr Thr Ala Gln Leu Thr Arg Glu Val Tyr Thr Asp
                405                 410                 415

GCA ATT GGG ACA GTA CAT CCG CAT CCA AGT TTT ACA AGT ACG ACT TGG             1296
Ala Ile Gly Thr Val His Pro His Pro Ser Phe Thr Ser Thr Thr Trp
                420                 425                 430

TAT AAT AAT AAT GCA CCT TCG TTC TCT GCC ATA GAG GCT GCT GTT GTT             1344
Tyr Asn Asn Asn Ala Pro Ser Phe Ser Ala Ile Glu Ala Ala Val Val
                435                 440                 445

CGA AAC CCG CAT CTA CTC GAT TTT CTA GAA CAA GTT ACA ATT TAC AGC             1392
Arg Asn Pro His Leu Leu Asp Phe Leu Glu Gln Val Thr Ile Tyr Ser
450                 455                 460

TTA TTA AGT CGA TGG AGT AAC ACT CAG TAT ATG AAT ATG TGG GGA GGA             1440
Leu Leu Ser Arg Trp Ser Asn Thr Gln Tyr Met Asn Met Trp Gly Gly
```

-continued

| | | | |
|---|---|---|---|
| 465 | 470 | 475 | 480 |

```
CAT AAA CTA GAA TTC CGA ACA ATA GGA GGA ACG TTA AAT ATC TCA ACA    1488
His Lys Leu Glu Phe Arg Thr Ile Gly Gly Thr Leu Asn Ile Ser Thr
                    485                 490                 495

CAA GGA TCT ACT AAT ACT TCT ATT AAT CCT GTA ACA TTA CCG TTC ACT    1536
Gln Gly Ser Thr Asn Thr Ser Ile Asn Pro Val Thr Leu Pro Phe Thr
            500                 505                 510

TCT CGA GAC GTC TAT AGG ACT GAA TCA TTG GCA GGG CTG AAT CTA TTT    1584
Ser Arg Asp Val Tyr Arg Thr Glu Ser Leu Ala Gly Leu Asn Leu Phe
            515                 520                 525

TTA ACT CAA CCT GTT AAT GGA GTA CCT AGG GTT GAT TTT CAT TGG AAA    1632
Leu Thr Gln Pro Val Asn Gly Val Pro Arg Val Asp Phe His Trp Lys
        530                 535                 540

TTC GTC ACA CAT CCG ATC GCA TCT GAT AAT TTC TAT TAT CCA GGG TAT    1680
Phe Val Thr His Pro Ile Ala Ser Asp Asn Phe Tyr Tyr Pro Gly Tyr
545                 550                 555                 560

GCT GGA ATT GGG ACG CAA TTA CAG GAT TCA GAA AAT GAA TTA CCA CCT    1728
Ala Gly Ile Gly Thr Gln Leu Gln Asp Ser Glu Asn Glu Leu Pro Pro
                565                 570                 575

GAA GCA ACA GGA CAG CCA AAT TAT GAA TCT TAT AGT CAT AGA TTA TCT    1776
Glu Ala Thr Gly Gln Pro Asn Tyr Glu Ser Tyr Ser His Arg Leu Ser
            580                 585                 590

CAT ATA GGA CTC ATT TCA GCA TCA CAT GTG AAA GCA TTG GTA TAT TCT    1824
His Ile Gly Leu Ile Ser Ala Ser His Val Lys Ala Leu Val Tyr Ser
        595                 600                 605

TGG ACG CAT CGT AGT GCA GAT CGT ACA AAT ACA ATT GAG CCA AAT AGC    1872
Trp Thr His Arg Ser Ala Asp Arg Thr Asn Thr Ile Glu Pro Asn Ser
        610                 615                 620

ATT ACA CAA ATA CCA TTA GTA AAA GCT TTC AAT CTG TCT TCA GGT GCC    1920
Ile Thr Gln Ile Pro Leu Val Lys Ala Phe Asn Leu Ser Ser Gly Ala
625                 630                 635                 640

GCT GTA GTG AGA GGA CCA GGA TTT ACA GGT GGG GAT ATC CTT CGA AGA    1968
Ala Val Val Arg Gly Pro Gly Phe Thr Gly Gly Asp Ile Leu Arg Arg
                645                 650                 655

ACG AAT ACT GGT ACA TTT GGG GAT ATA CGA GTA AAT ATT AAT CCA CCA    2016
Thr Asn Thr Gly Thr Phe Gly Asp Ile Arg Val Asn Ile Asn Pro Pro
            660                 665                 670

TTT GCA CAA AGA TAT CGC GTG AGG ATT CGC TAT GCT TCT ACC ACA GAT    2064
Phe Ala Gln Arg Tyr Arg Val Arg Ile Arg Tyr Ala Ser Thr Thr Asp
            675                 680                 685

TTA CAA TTC CAT ACG TCA ATT AAC GGT AAA GCT ATT AAT CAA GGT AAT    2112
Leu Gln Phe His Thr Ser Ile Asn Gly Lys Ala Ile Asn Gln Gly Asn
        690                 695                 700

TTT TCA GCA ACT ATG AAT AGA GGA GAG GAC TTA GAC TAT AAA ACC TTT    2160
Phe Ser Ala Thr Met Asn Arg Gly Glu Asp Leu Asp Tyr Lys Thr Phe
705                 710                 715                 720

MGA ACT GTA GGC TTT ACC ACT CCA TTT AGC TTT TTA GAT GTA CAA AGT    2208
Arg Thr Val Gly Phe Thr Thr Pro Phe Ser Phe Leu Asp Val Gln Ser
                725                 730                 735

ACA TTC ACA ATA GGT GCT TGG AAC TTC TCT TCA GGT AAC GAA GTT TAT    2256
Thr Phe Thr Ile Gly Ala Trp Asn Phe Ser Ser Gly Asn Glu Val Tyr
            740                 745                 750

ATA GAT AGA ATT GAA TTT GTT CCG GTA GAA GTA ACA TAT GAG GCA GAA    2304
Ile Asp Arg Ile Glu Phe Val Pro Val Glu Val Thr Tyr Glu Ala Glu
            755                 760                 765

TAT GAT TTT GAA AAA GCG CAA GAG AAG GTT ACT GCA CTG TTT ACA TCT    2352
Tyr Asp Phe Glu Lys Ala Gln Glu Lys Val Thr Ala Leu Phe Thr Ser
        770                 775                 780

ACG AAT CCA AGA GGA TTA AAA ACA GAT GTA AAG GAT TAT CAT ATT GAC    2400
Thr Asn Pro Arg Gly Leu Lys Thr Asp Val Lys Asp Tyr His Ile Asp
```

-continued

| | | | | | | | | | | | | | | | | |
|---|---|---|---|---|---|---|---|---|---|---|---|---|---|---|---|---|
| 785 | | | | | 790 | | | | | 795 | | | | | 800 | |
| CAG | GTA | TCA | AAT | TTA | GTA | GAG | TCT | CTA | TCA | GAT | GAA | TTC | TAT | CTT | GAT | 2448 |
| Gln | Val | Ser | Asn | Leu | Val | Glu | Ser | Leu | Ser | Asp | Glu | Phe | Tyr | Leu | Asp | |
| | | | | 805 | | | | | 810 | | | | | 815 | | |
| GAA | AAG | AGA | GAA | TTA | TTC | GAG | ATA | GTT | AAA | TAC | GCG | AAG | CAA | CTC | CAT | 2496 |
| Glu | Lys | Arg | Glu | Leu | Phe | Glu | Ile | Val | Lys | Tyr | Ala | Lys | Gln | Leu | His | |
| | | | | 820 | | | | | 825 | | | | | 830 | | |
| ATT | GAG | CGT | AAC | ATG | TAG | AAT | TAA | AAT | CTA | CCT | AAA | TCC | AGA | AAA | ATA | 2544 |
| Ile | Glu | Arg | Asn | Met | * | Asn | * | Asn | Leu | Pro | Lys | Ser | Arg | Lys | Ile | |
| | | | | 835 | | | | | 840 | | | | | 845 | | |
| AAA | GGG | TTA | AAT | ATA | CAA | TTC | TTG | TAC | CAA | TAT | TTT | GAG | TGA | TTA | GAT | 2592 |
| Lys | Gly | Leu | Asn | Ile | Gln | Phe | Leu | Tyr | Gln | Tyr | Phe | Glu | * | Leu | Asp | |
| | | | | 850 | | | | | 855 | | | | | 860 | | |
| GTA | GGA | TGA | AAT | TTA | ATT | GTA | TGC | TAT | TTA | ACA | GTA | GAG | ATA | TTA | AAA | 2640 |
| Val | Gly | * | Asn | Leu | Ile | Val | Cys | Tyr | Leu | Thr | Val | Glu | Ile | Leu | Lys | |
| 865 | | | | | 870 | | | | | 875 | | | | | 880 | |
| ATT | AAT | TTA | TCT | ATA | CAT | TAA | TAG | TAT | AGA | CAT | ACA | AAC | ATA | AGA | GAG | 2688 |
| Ile | Asn | Leu | Ser | Ile | His | * | * | Tyr | Arg | His | Thr | Asn | Ile | Arg | Glu | |
| | | | | 885 | | | | | 890 | | | | | 895 | | |
| CAT | TGT | CTT | TTC | GTA | GGC | TAC | AAT | GCT | CTC | TAT | TTA | CTA | TTT | ATT | TTT | 2736 |
| His | Cys | Leu | Phe | Val | Gly | Tyr | Asn | Ala | Leu | Tyr | Leu | Leu | Phe | Ile | Phe | |
| | | | | 900 | | | | | 905 | | | | | 910 | | |
| CTT | TTG | TAT | CTT | CAA | ATT | GAC | GTT | GTT | CTA | AGC | GTT | CTA | TTG | CAG | CTC | 2784 |
| Leu | Leu | Tyr | Leu | Gln | Ile | Asp | Val | Val | Leu | Ser | Val | Leu | Leu | Gln | Leu | |
| | | | | 915 | | | | | 920 | | | | | 925 | | |
| GTC | GTT | TAG | TAT | CAT | CAA | TGT | TTG | TAT | AAA | GAG | ATG | TTG | TTT | CCA | TAG | 2832 |
| Val | Val | * | Tyr | His | Gln | Cys | Leu | Tyr | Lys | Glu | Met | Leu | Phe | Pro | * | |
| | | | | 930 | | | | | 935 | | | | | 940 | | |
| AAT | TAT | GTC | CCA | TTT | GAT | TTG | CTA | ATA | ATA | CTA | AAT | CTT | TAT | TTT | CAT | 2880 |
| Asn | Tyr | Val | Pro | Phe | Asp | Leu | Leu | Ile | Ile | Leu | Asn | Leu | Tyr | Phe | His | |
| 945 | | | | | 950 | | | | | 955 | | | | | 960 | |
| TAT | AGT | GAT | TAG | TAG | CAT | AAG | TAT | GAC | GTA | ATT | TAT | GAG | GGC | TTT | TCT | 2928 |
| Tyr | Ser | Asp | * | * | His | Lys | Tyr | Asp | Val | Ile | Tyr | Glu | Gly | Phe | Ser | |
| | | | | 965 | | | | | 970 | | | | | 975 | | |
| TTT | CAT | CAA | AAG | CCC | TTG | TGT | ATT | TCT | CTG | TAA | GCT | T | | | | 2965 |
| Phe | His | Gln | Lys | Pro | Leu | Cys | Ile | Ser | Leu | * | Ala | | | | | |
| | | | | 980 | | | | | 985 | | | | | | | |